US012597125B2

(12) United States Patent
Hirayama et al.

(10) Patent No.: US 12,597,125 B2
(45) Date of Patent: Apr. 7, 2026

(54) APPARATUS AND METHOD FOR CORRECTING A CONTOUR OF AN OBJECT IN A MEDICAL IMAGE

(71) Applicant: Canon Medical Systems Corporation, Otawara (JP)

(72) Inventors: Kodai Hirayama, Nasushiobara (JP); Yasuhiko Abe, Otawara (JP); Koji Ando, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 280 days.

(21) Appl. No.: 17/661,083

(22) Filed: Apr. 28, 2022

(65) Prior Publication Data

US 2022/0358643 A1 Nov. 10, 2022

(30) Foreign Application Priority Data

May 7, 2021 (JP) ................................. 2021-078947

(51) Int. Cl.
*G06T 7/00* (2017.01)
*A61B 8/00* (2006.01)
(Continued)

(52) U.S. Cl.
CPC .......... *G06T 7/0012* (2013.01); *A61B 8/0883* (2013.01); *A61B 8/461* (2013.01);
(Continued)

(58) Field of Classification Search
CPC ..................... G06T 7/0012; G06T 7/13; G06T 2207/10132; G06T 2207/20096;
(Continued)

(56) References Cited

U.S. PATENT DOCUMENTS 7,022,075 B2 * 4/2006 Grunwald .............. A61B 8/465
600/446
8,055,075 B1 * 11/2011 Tamura .................... G06T 7/13
382/199
(Continued)

FOREIGN PATENT DOCUMENTS

JP 2010-259656 A 11/2010
JP 2011-036282 A * 2/2011
(Continued)

OTHER PUBLICATIONS

English Translation of Japanese Office Action issued Oct. 1, 2024 in Japanese Patent Application No. 2021-78947 (4 pages) ( Year: 2024).*

(Continued)

*Primary Examiner* — Scott A Rogers
(74) *Attorney, Agent, or Firm* — Oblon, McClelland, Maier & Neustadt, L.L.P.

(57) ABSTRACT

According to one embodiment, there is provided a medical image processing apparatus and method for estimating a contour of a desired structure, such as a cardiac muscle, based on a medical image, such as an ultrasound image, and cross section information of the desired structure, receiving a desired correction mode from among multiple correction modes for correcting the estimated contour, each of the multiple correction modes having a correction amount set corresponding to the information on the cross section, and correcting the estimated contour according to the desired correction mode.

16 Claims, 25 Drawing Sheets

(51) Int. Cl.

| | | |
|---|---|---|
| *A61B 8/08* | (2006.01) | |
| *G06N 20/00* | (2019.01) | |
| *G06T 7/13* | (2017.01) | |

(52) U.S. Cl.
CPC ............... *G06N 20/00* (2019.01); *G06T 7/13* (2017.01); *A61B 8/481* (2013.01); *A61B 8/5269* (2013.01); *A61B 2576/023* (2013.01); *G06T 2207/10132* (2013.01); *G06T 2207/20096* (2013.01); *G06T 2207/30048* (2013.01)

(58) Field of Classification Search
CPC .......... G06T 2207/30048; G06N 20/00; A61B 8/0883; A61B 8/461; A61B 8/481; A61B 8/5269; A61B 2576/023
See application file for complete search history.

(56) References Cited

U.S. PATENT DOCUMENTS

| | | | | |
|---|---|---|---|---|
| 8,986,215 | B2 * | 3/2015 | Masumoto | ............. G16H 50/30 |
| | | | | 382/131 |
| 9,072,489 | B2 * | 7/2015 | Chono | ................... A61B 8/461 |
| 9,072,490 | B2 * | 7/2015 | Sakaguchi | ............. A61B 6/507 |
| 9,171,220 | B2 * | 10/2015 | Wang | .................. A61B 8/5223 |
| 9,357,981 | B2 * | 6/2016 | Toma | ................... A61B 8/5223 |
| 9,993,215 | B2 * | 6/2018 | Lou | ....................... G06T 11/005 |
| 10,292,684 | B2 * | 5/2019 | Okazaki | ................... A61B 6/12 |
| 10,521,906 | B2 * | 12/2019 | Forman | ................. G16H 50/20 |
| 11,484,286 | B2 * | 11/2022 | Wissel | ................. A61B 8/5238 |
| 11,707,201 | B2 * | 7/2023 | Pinkovich | ............ A61B 5/7267 |
| | | | | 600/511 |
| 11,744,554 | B2 * | 9/2023 | White | .................. A61B 8/5223 |
| | | | | 600/443 |
| 2004/0022438 | A1 * | 2/2004 | Hibbard | ................ G06T 7/0012 |
| | | | | 382/199 |
| 2013/0184570 | A1 | 7/2013 | Wang et al. | |
| 2015/0206323 | A1 * | 7/2015 | Lee | ......................... A61B 6/032 |
| | | | | 382/107 |
| 2016/0224229 | A1 | 8/2016 | Jo et al. | |
| 2018/0218497 | A1 * | 8/2018 | Golden | ................... G06T 7/136 |
| 2020/0037992 | A1 * | 2/2020 | Oyama | ................. A61B 8/468 |
| 2020/0193603 | A1 * | 6/2020 | Golden | ................... G06T 7/149 |
| 2020/0315582 | A1 * | 10/2020 | Waechter-Stehle | ......................... G06T 7/0012 |
| 2022/0375099 | A1 * | 11/2022 | Schulz | ................. G06T 7/0012 |
| 2025/0120677 | A1 * | 4/2025 | Abe | ..................... A61B 8/0858 |

FOREIGN PATENT DOCUMENTS

| | | | |
|---|---|---|---|
| JP | 2013-22463 | A | 2/2013 |
| JP | 2013111434 | A * | 6/2013 |
| JP | 2015-226711 | A | 12/2015 |
| JP | 2018-51001 | A | 4/2018 |
| JP | 2019-88458 | A | 6/2019 |
| WO | WO 2011/125513 | A1 | 10/2011 |
| WO | WO 2013/094205 | A1 | 6/2013 |

OTHER PUBLICATIONS

JPO Reasons for Refusal in Japanese patent application No. 2021-078947 issued Mar. 18, 2025 (translation).*

Amended claims in Japanese patent application No. 2021-078947 filed Jul. 17, 2025 (translation).*

JPO Written Opinion in Japanese patent application No. 2021-078947 issued Jul. 17, 2025 (translation).*

Japanese Office Action issued Oct. 1, 2024 in Japanese Patent Application No. 2021-078947, 4 pages.

Japanese Office Action issued Mar. 18, 2025 in Japanese Patent Application No. 2021-078947, citing references 15-18 therein, 5 pages.

* cited by examiner

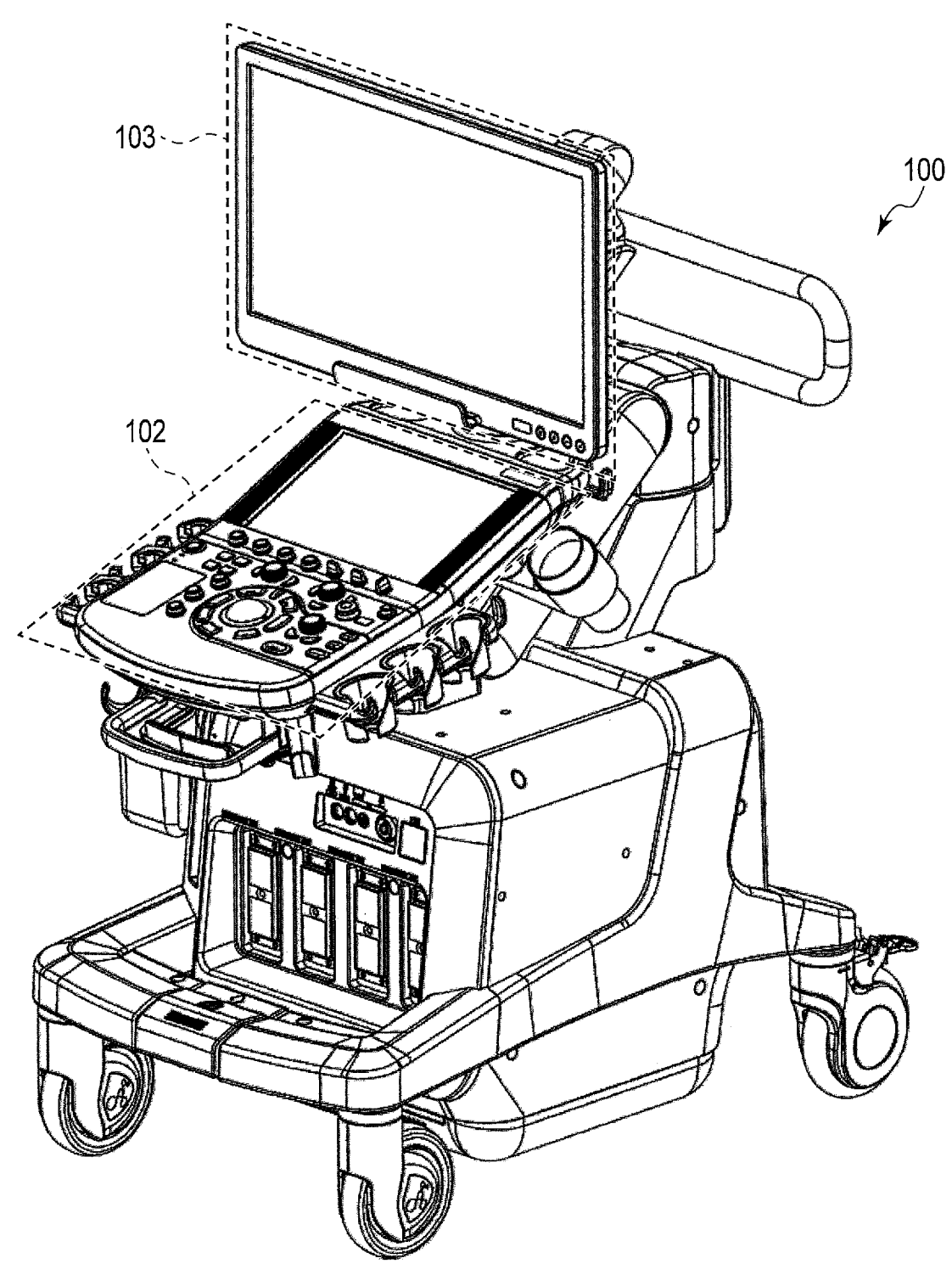
F I G. 2

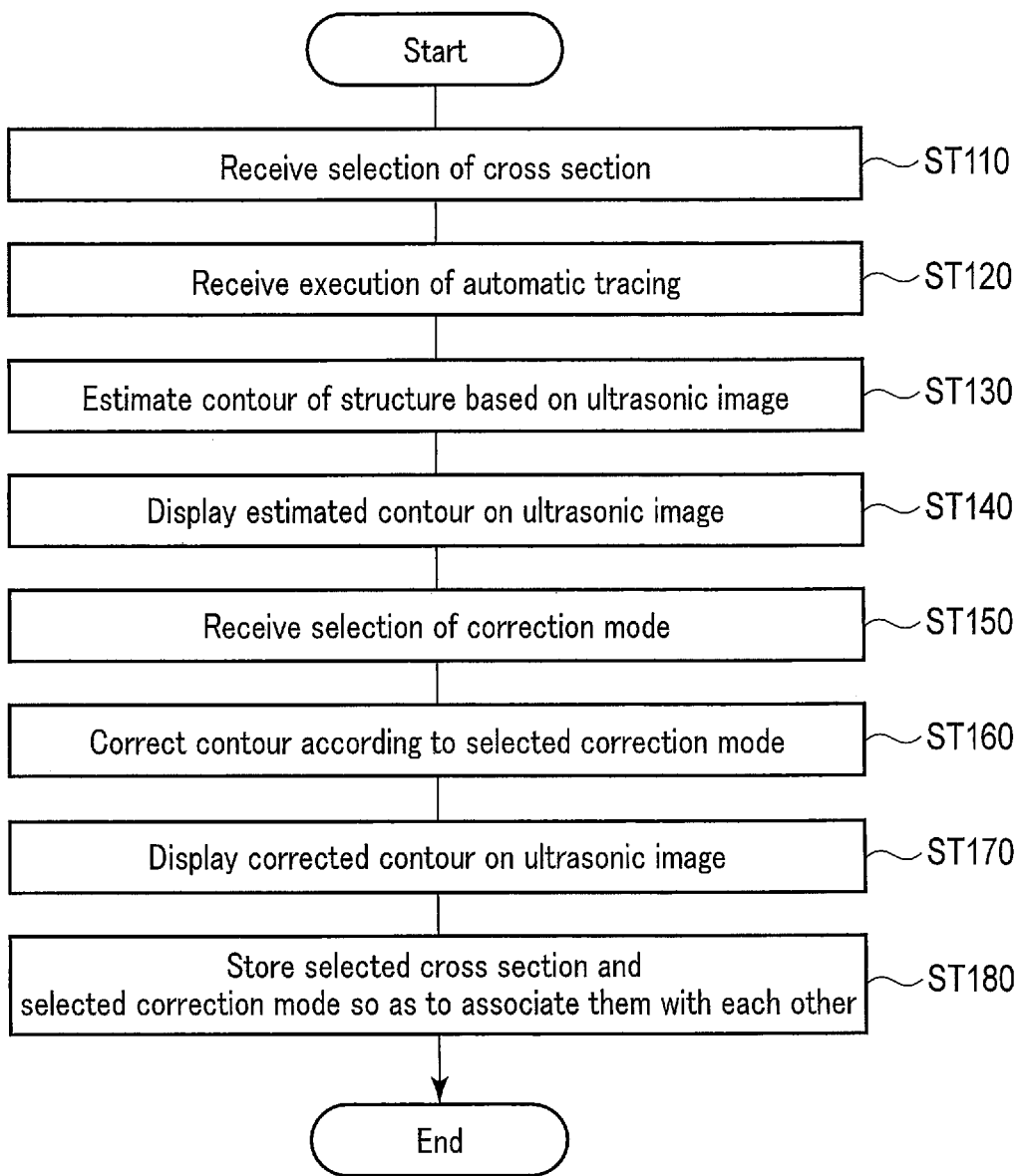

Start

Receive selection of cross section — ST110

Receive execution of automatic tracing — ST120

Estimate contour of structure based on ultrasonic image — ST130

Display estimated contour on ultrasonic image — ST140

Receive selection of correction mode — ST150

Correct contour according to selected correction mode — ST160

Display corrected contour on ultrasonic image — ST170

Store selected cross section and selected correction mode so as to associate them with each other — ST180

End

F I G. 4

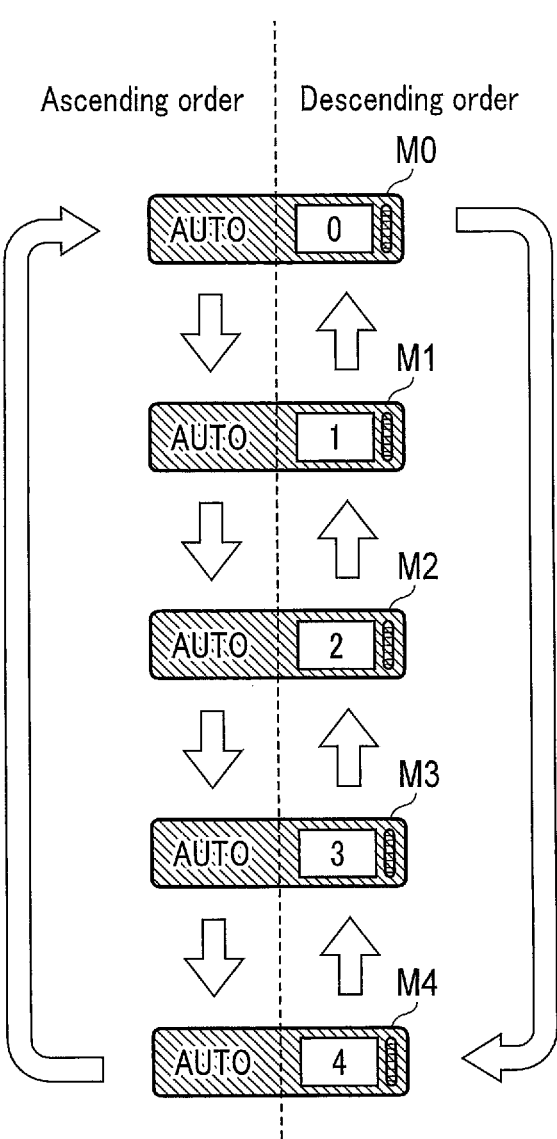
F I G. 11

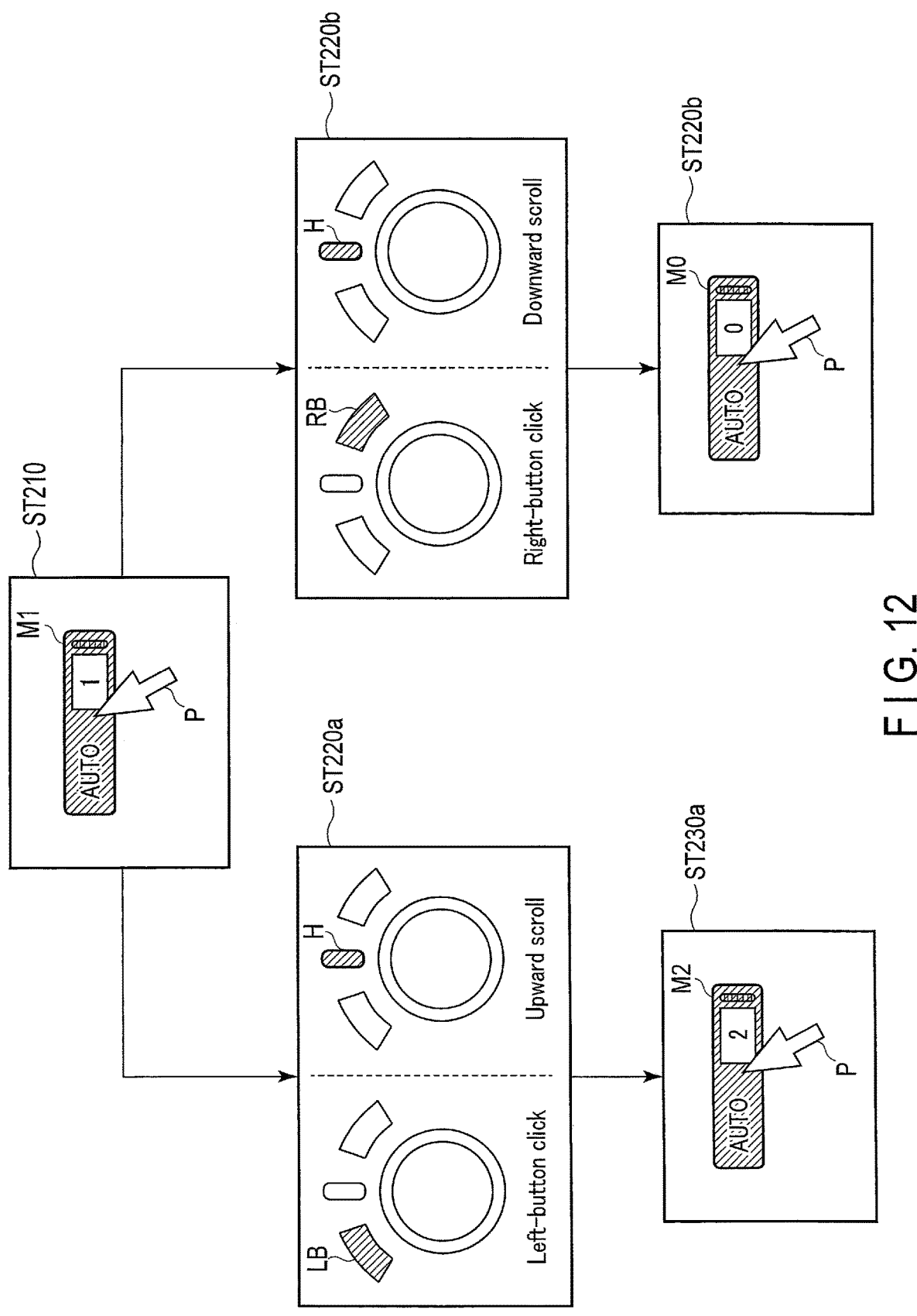
F I G. 12

F I G. 13

300
| Correction mode | Direction | Correction amount |
|---|---|---|
| M1 | Upward | 3 |
| M2 | Right | 3 |
| M3 | Upward | 3 |
| M4 | Right | 3 |
F I G. 14
310
| Direction | Point | Correction amount |
|---|---|---|
| Right | Po1 | 0 |
| Right | Po2 | 0 |
| Right | Po3 | 0 |
| Upward | Po4 | 3 |
| Left | Po5 | 0 |
| Left | Po6 | 0 |
| Left | Po7 | 0 |
F I G. 15

320
| Direction | Point | Correction amount |
|-----------|-------|-------------------|
| Right | Po1 | 3 |
| Right | Po2 | 3 |
| Right | Po3 | 3 |
| Upward | Po4 | 0 |
| Left | Po5 | 0 |
| Left | Po6 | 0 |
| Left | Po7 | 0 |
F I G. 16

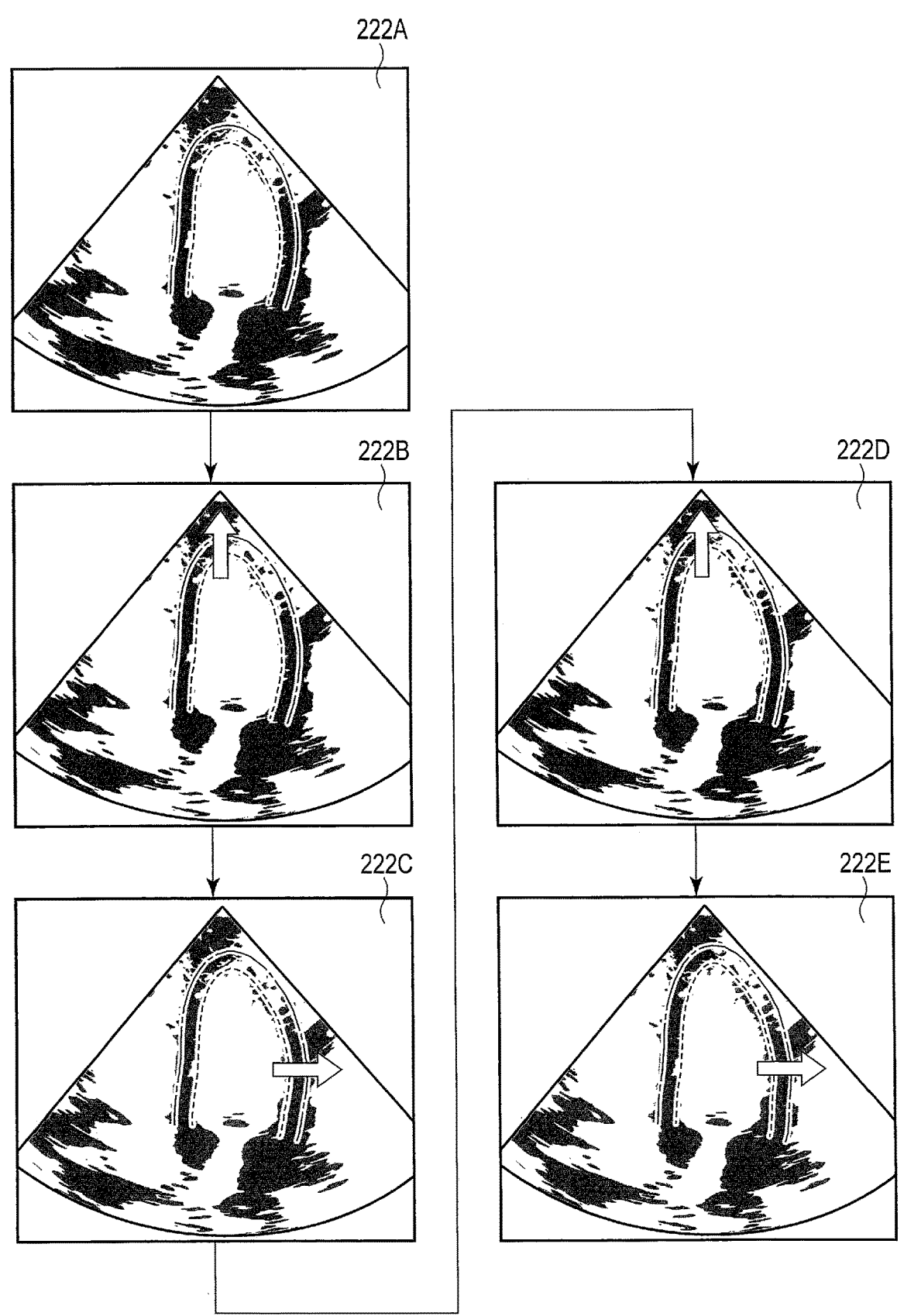
F I G. 17

320A
| Direction | Point | Correction amount |
|---|---|---|
| Right | Po1 | 1 |
| Right | Po2 | 3 |
| Right | Po3 | 3 |
| Upward | Po4 | 0 |
| Left | Po5 | 0 |
| Left | Po6 | 0 |
| Left | Po7 | 0 |
F I G. 18
300A
| Correction mode | Direction | Correction amount |
|---|---|---|
| M1 | Upward | 5 |
| M2 | Right | 3 |
| M3 | Upward | 5 |
| M4 | Right | 3 |
F I G. 19

300B

| Correction mode | Direction | Correction amount (inward) | Correction amount (outward) |
|:---:|:---:|:---:|:---:|
| M1 | Upward | 3 | 4 |
| M2 | Right | 3 | 4 |
| M3 | Upward | 3 | 4 |
| M4 | Right | 3 | 4 |

F I G. 20

400

| Cross section | Correction mode |
|---|---|
| Apical-2Ch | M3 |
| Apical-3Ch | M1 |
| Apical-4Ch | M2 |

F I G. 22

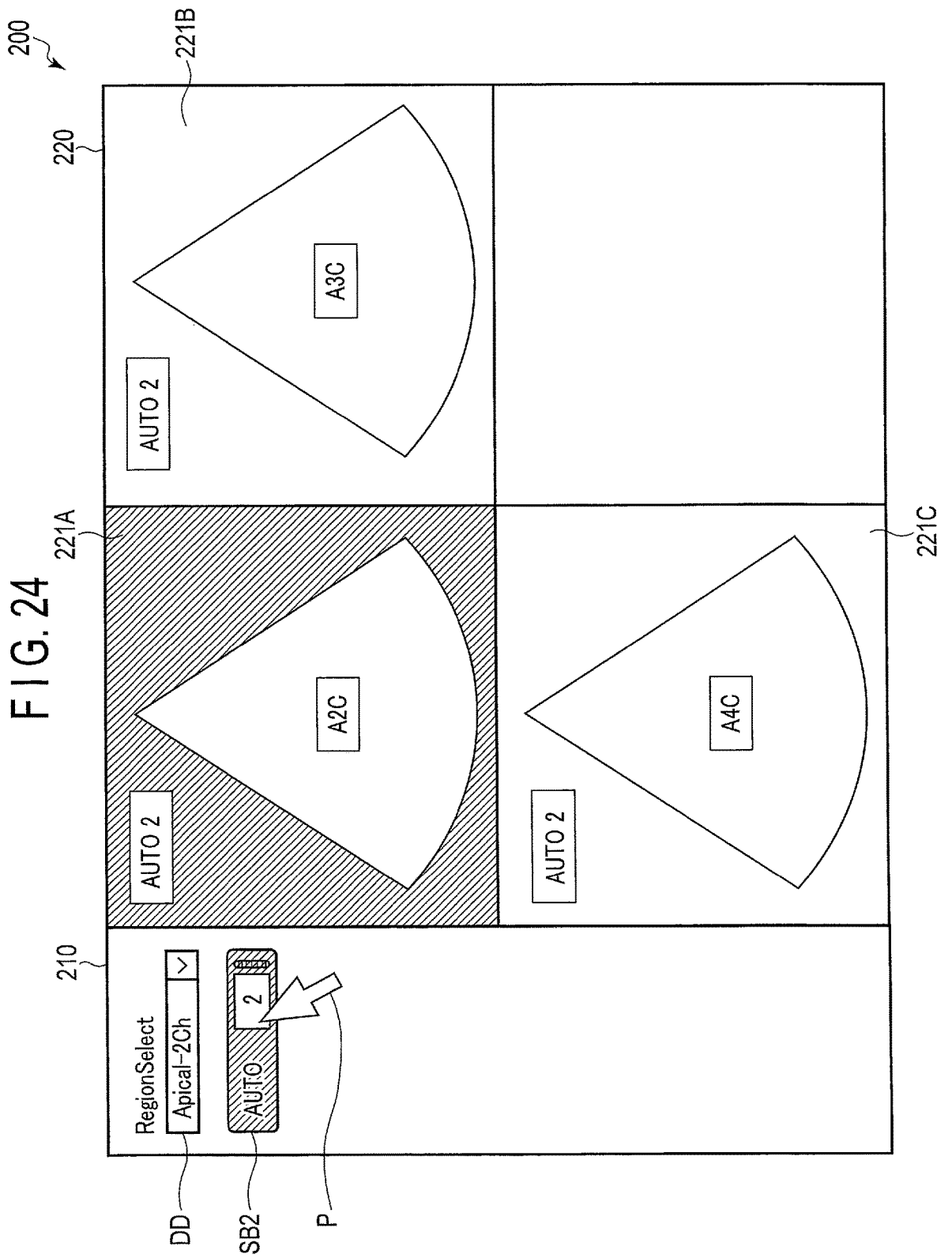
F I G. 24

300C
| Correction mode | Direction | Correction amount |
|:---:|:---:|:---:|
| M1 | Inward | -3 |
| M2 | Inward | -3 |
| M3 | Inward | -3 |
| M4 | Inward | -3 |
F I G. 25

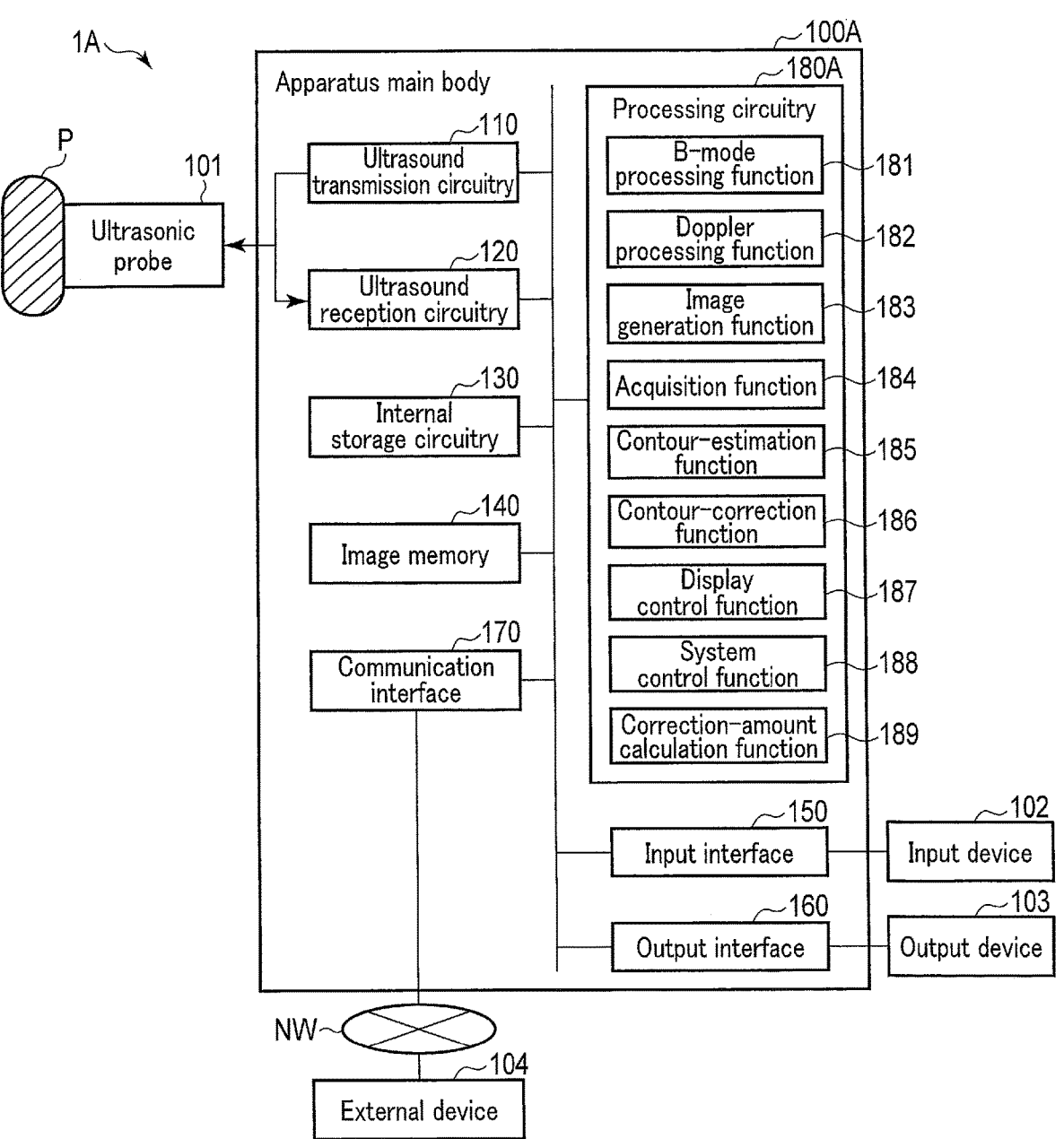
F I G. 26

300D

| Correction mode | Direction | Correction amount |
|---|---|---|
| M1 | Upward | 2 |
| M2 | Right | 2 |
| M3 | Upward | 2 |
| M4 | Right | 2 |

F I G. 28

300E

| Correction mode | Direction | Correction amount (default) | Correction amount (changed) |
|---|---|---|---|
| M1 | Upward | 3 | 2 |
| M2 | Right | 3 | 2 |
| M3 | Upward | 3 | 2 |
| M4 | Right | 3 | 2 |

F I G. 29

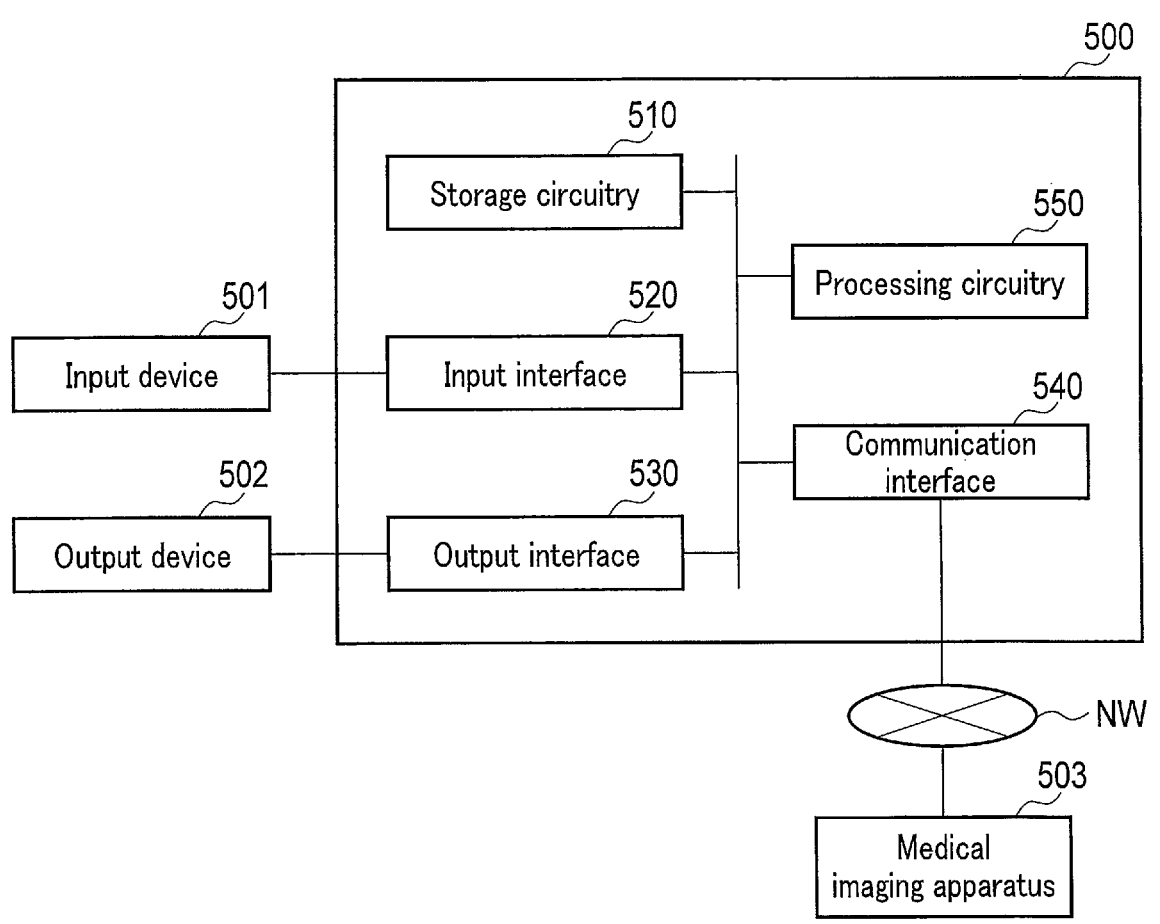
F I G. 30

APPARATUS AND METHOD FOR CORRECTING A CONTOUR OF AN OBJECT IN A MEDICAL IMAGE

CROSS-REFERENCE TO RELATED APPLICATIONS

This application is based upon and claims the benefit of priority from Japanese Patent Application No. 2021-078947, filed May 7, 2021, the entire contents of which are incorporated herein by reference.

FIELD

Embodiments described herein relate generally to a medical image processing apparatus, an ultrasonic diagnosis apparatus, and a method.

BACKGROUND

When acquiring an ejection fraction (EF) of the left ventricle through a myocardial function analysis, a contour of the cardiac muscle to be traced is set in order to trace the cardiac muscle. There is as conventional art a function of automatically estimating the contour of the cardiac muscle through artificial intelligence (AI).

Although it is possible to automatically estimate the contour with the conventional art, some users operate a trackball or the like to make an adjustment. With regard to the adjustment, there are various patterns of adjustment amount and adjustment site for the contour depending on the cross section of the structure. As a result, the operation performed until a contour desired by a user is set may become complicated.

BRIEF DESCRIPTION OF THE DRAWINGS

FIG. 2 is an external perspective view of an apparatus main body of the ultrasonic diagnosis apparatus according to the first embodiment.

FIG. 4 is a flowchart for explaining operations of processing circuitry that executes contour-setting processing according to the first embodiment.

FIG. 11 is a diagram for explaining transition of multiple correction modes according to the first embodiment.

FIG. 12 is a diagram for explaining a method of switching the correction modes according to the first embodiment.

FIG. 13 is a diagram for explaining multiple points defining a contour according to the first embodiment.

FIG. 14 is a diagram showing an example of a table associating the correction modes, the directions, and the correction amounts with one another according to the first embodiment.

FIG. 15 is a diagram for showing an example of a table associating the directions, the points, and the correction amounts in connection with the correction mode M1 shown in the table in FIG. 14.

FIG. 16 is a diagram for showing an example of a table associating the directions, the points, and the correction amounts in connection with the correction mode M2 shown in the table in FIG. 14.

FIG. 17 is a diagram for explaining transition of multiple corrected contours corresponding to the multiple correction modes according to the first embodiment.

FIG. 18 is a diagram showing another example of the table shown in FIG. 16.

FIG. 19 is a diagram showing another example of the table shown in FIG. 14.

FIG. 20 is a diagram showing another example of the table shown in FIG. 14.

FIG. 22 is a diagram showing an example of a table associating cross sections and the correction modes with each other according to the first embodiment.

FIG. 24 is a diagram showing an example of a display screen posterior to execution of the contour-correction processing according to the first application example, of the first embodiment.

FIG. 25 is a diagram showing an example of a table associating the correction modes, the directions, and the correction amounts with one another according to a second application example of the first embodiment.

FIG. 26 is a block diagram showing a configuration example of an ultrasonic diagnosis apparatus according to a second embodiment.

FIG. 28 is a diagram showing another example of the table shown in FIG. 14, in which the correction amounts have been changed through correction-amount-calculation processing according the second embodiment.

FIG. 29 is a diagram showing another example of the table shown in FIG. 28.

FIG. 30 is a block diagram showing a configuration example of a medical image processing apparatus according to a third embodiment.

DETAILED DESCRIPTION

In general, according to one embodiment, a medical image processing apparatus includes processing circuitry. The processing circuitry estimates a contour of a desired structure based on a medical image, receives a desired correction mode among multiple correction modes for correcting the estimated contour, and corrects the estimated contour according to the desired correction mode.

Hereinafter, embodiments of an ultrasonic diagnosis apparatus and a medical image processing apparatus will be described in detail with reference to the accompanying drawings.

First Embodiment

Figure 1:
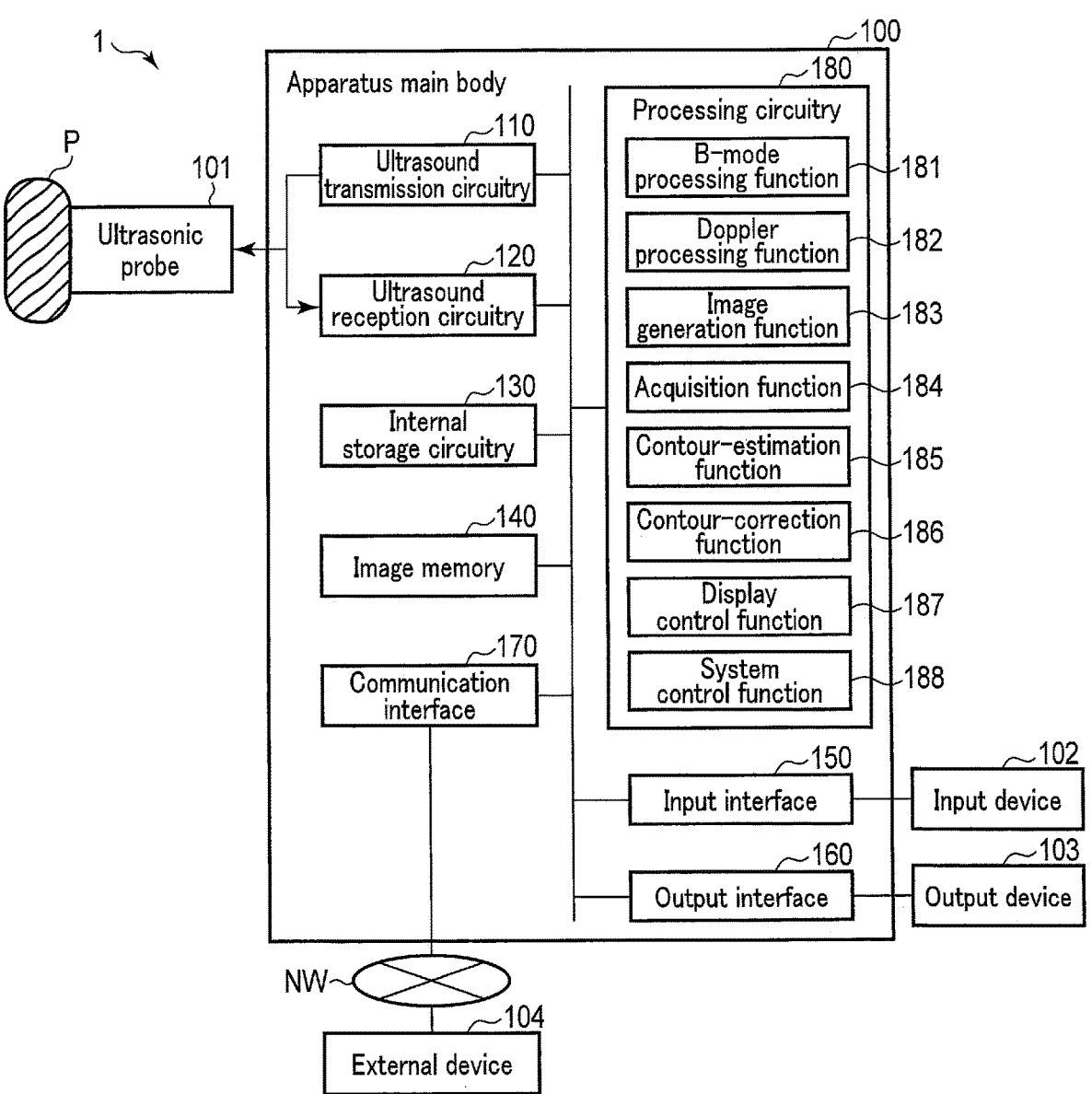
FIG. 1 is a block diagram showing a configuration example of an ultrasonic diagnosis apparatus according to a first embodiment.

FIG. 1 is a block diagram showing a configuration example of an ultrasonic diagnosis apparatus according to a first embodiment. An ultrasonic diagnosis apparatus 1 shown in FIG. 1 includes an apparatus main body 100 and an ultrasonic probe 101. The apparatus main body 100 is connected to an input device 102 and an output device 103. The apparatus main body 100 is also connected to an external device 104 via a network NW. The external device 104 is, for example, a server equipped with a picture archiving and communication systems (PACS).

The ultrasonic probe 101 performs ultrasonic scanning in a scan area of a living body P, which is a subject, under the control of, for example, the apparatus main body 100. The ultrasonic probe 101 includes, for example, a plurality of piezoelectric transducers, a matching layer provided between a case and each of the piezoelectric transducers, and a backing material that prevents ultrasonic waves from propagating backward with respect to a direction of radiation from the piezoelectric transducers. The ultrasonic probe 101 is a two-dimensional array probe in which a plurality of ultrasonic transducers are aligned along, for example, a first element alignment direction (elevation direction) and a second element alignment direction (azimuth direction). The ultrasonic probe 101 is detachably connected to the apparatus main body 100. The ultrasonic probe 101 may be provided with buttons which are pressed when offset processing, an operation for freezing an ultrasonic image (freeze operation), and the like are performed.

The piezoelectric transducers generate ultrasonic waves based on a drive signal supplied from ultrasound transmission circuitry 110 (described later) that is included in the apparatus main body 100. Ultrasonic waves are thereby transmitted from the ultrasonic probe 101 to the living body P. When ultrasonic waves are transmitted from the ultrasonic probe 101 to the living body P, the transmitted ultrasonic waves are sequentially reflected on the acoustic impedance discontinuous surfaces of the body tissue of the living body P, and are received as reflection wave signals by the plurality of piezoelectric transducers. The amplitude of the received reflection wave signals depends on the difference in the acoustic impedance on the discontinuous surfaces from which the ultrasonic waves are reflected. If the transmitted ultrasonic pulse is reflected from the surface of, for example, a moving bloodstream or a cardiac wall, the frequency of the resultant reflection wave signal will be shifted due to the Doppler effect, with the shift depending on the velocity component in the ultrasonic transmission direction of the moving object. The ultrasonic probe 101 receives the reflection wave signals from the living body P, and converts them into electric signals.

FIG. 1 shows an example of a connection relationship between a single ultrasonic probe 101 and the apparatus main body 100. However, a plurality of ultrasonic probes may be connected to the apparatus main body 100. Which of the connected ultrasonic probes is to be used for the ultrasonic scanning can be determined discretionarily through, for example, a software button on a touch panel (described later).

The apparatus main body 100 generates an ultrasonic image based on the reflection wave signals received by the ultrasonic probe 101. The apparatus main body 100 includes the aforementioned ultrasound transmission circuitry 110, ultrasound reception circuitry 120, internal storage circuitry 130, an image memory 140, an input interface 150, an output interface 160, a communication interface 170, and processing circuitry 180.

The ultrasound transmission circuitry 110 is a processor that supplies a drive signal to the ultrasonic probe 101. The ultrasound transmission circuitry 110 is implemented by, for example, trigger generation circuitry, delay circuitry, and pulser circuitry. The trigger generation circuitry repeatedly generates rate pulses for forming transmission ultrasonic waves at a predetermined rate frequency. The delay circuitry gives each rate pulse generated by the trigger generation circuitry a delay time for each piezoelectric transducer needed to converge the ultrasonic waves generated from the ultrasonic probe into a beam and determine the transmission directivity. The pulser circuitry applies a drive signal (drive pulse) to the multiple ultrasound transducers of the ultrasonic probe 101 at a timing based on the rate pulse. By varying the delay time provided to each rate pulse by the delay circuitry, the transmission direction from the surfaces of the piezoelectric transducers can be discretionarily adjusted.

The ultrasound transmission circuitry 110 can discretionarily change the output intensity of the ultrasonic waves through the drive signal. In the ultrasonic diagnosis apparatus, the influence of the attenuation of the ultrasonic waves in the living body P can be reduced by increasing the output intensity. By reducing the influence of the attenuation of the ultrasonic waves, the ultrasonic diagnosis apparatus can obtain a reflection wave signal having a large S/N ratio when receiving the signal.

In general, when the ultrasonic waves are propagated inside the living body P, the magnitude of the oscillation of the ultrasonic waves corresponding to the output intensity (the magnitude is also referred to as "acoustic power") is attenuated. The attenuation of the acoustic power is caused by absorption, scattering, reflection, etc. The degree of attenuation of the acoustic power depends on the frequency of the ultrasonic waves and the distance of the ultrasonic waves in the radial direction. For example, the degree of attenuation is increased by increasing the frequency of the ultrasonic waves. Also, the longer the distance of the ultrasonic waves in the radiation direction, the larger the degree of attenuation.

The ultrasound reception circuitry 120 is a processor that performs various types of processing on the reflection wave signals received by the ultrasonic probe 101 and generates reception signals. The ultrasound reception circuitry 120 generates reception signals based on the reflection wave signals of the ultrasonic waves acquired by the ultrasonic probe 101. Specifically, the ultrasound reception circuitry 120 is implemented by, for example, a preamplifier, an A/D converter, a demodulator, and a beam former. The preamplifier performs gain correction processing by amplifying the reflection wave signals received by the ultrasonic probe 101 for each channel. The A/D converter converts the gain-corrected reflection wave signals into digital signals. The demodulator demodulates the digital signals. The beam former, for example, gives the demodulated digital signals a delay time needed to determine the reception directivity, and adds a plurality of digital signals given the delay time. Through the addition processing by the beam former, reception signals with an enhanced reflection component in a direction corresponding to the reception directivity are generated.

The internal storage circuitry 130 includes, for example, a magnetic storage medium, an optical storage medium, or a processor-readable storage medium such as a semiconductor memory. The internal storage circuitry 130 stores a program for implementing ultrasound transmission-reception, a program related to myocardial function analysis (described later), various data, etc. The various data include, for example, a look-up table (LUT) and parameters used during execution of the programs. For example, the programs and various data may be pre-stored in the internal storage circuitry 130. Alternatively, the programs and various data may be stored and distributed in a non-transitory storage medium, read from the non-transitory storage medium, and installed in the internal storage circuitry 130. The internal storage circuitry 130 stores B-mode image data, contrast image data, image data related to a bloodstream image, and the like that are generated by the processing circuitry 180, in accordance with an operation input via the input interface 150. The internal storage circuitry 130 can also transfer the stored image data to the external device 104 or the like via the communication interface 170.

The internal storage circuitry 130 may be a drive or the like which reads and writes various types of information to and from a portable storage medium, such as a CD drive, a DVD drive, and a flash memory. The internal storage circuitry 130 can also write the stored data onto a portable storage medium and store the data in the external device 104 through the portable storage medium.

The image memory 140 includes, for example, a magnetic storage medium, an optical storage medium, or a processor-readable storage medium such as a semiconductor memory. The image memory 140 stores image data corresponding to a plurality of frames immediately before a freeze operation input via the input interface 150. The image data stored in the image memory 140 is, for example, continuously displayed (cine-displayed).

The internal storage circuitry 130 and the image memory 140 need not necessarily be implemented by independent storage devices. The internal storage circuitry 130 and the image memory 140 may be implemented by a single storage device. Each of the internal storage circuitry 130 and the image memory 140 may be implemented by a plurality of storage devices.

The input interface 150 receives various commands from an operator through the input device 102 (input unit). The input device 102 is, for example, a mouse, a keyboard, a panel switch, a slider switch, a trackball, a rotary encoder, an operation panel, or a touch panel. The input interface 150 is connected to the processing circuitry 180 via a bus, for example, thereby converting, into an electric signal, an operation command input by the operator and outputting the electric signal to the processing circuitry 180. The input interface 150 is not limited to a component that is connected to a physical operation component such as a mouse and keyboard. Examples of the input interface include circuitry which receives an electric signal corresponding to an operation command input from an external input device provided independently from the ultrasonic diagnosis apparatus 1, and outputs the electric signal to the processing circuitry 180.

The output interface 160 is an interface for outputting, for example, an electric signal from the processing circuitry 180 to the output device 103. The output device 103 is any display such as a liquid crystal display, an organic EL display, an LED display, a plasma display, or a CRT display. The output device 103 may be a touch-panel display that also serves as the input device 102. The output device 103 may further include a speaker that outputs voice in addition to a display. The output interface 160 is connected to the processing circuitry 180 via a bus, for example, and outputs an electric signal from the processing circuitry 180 to the output device 103.

FIG. 2 is an external perspective view of the apparatus main body of the ultrasonic diagnosis apparatus according to the first embodiment. In the apparatus main body 100 shown in FIG. 2, the input device 102 and the output device 103 are connected to each other. The user operates the input device 102 and obtains desired clinical information by viewing the output device 103.

Figure 3:
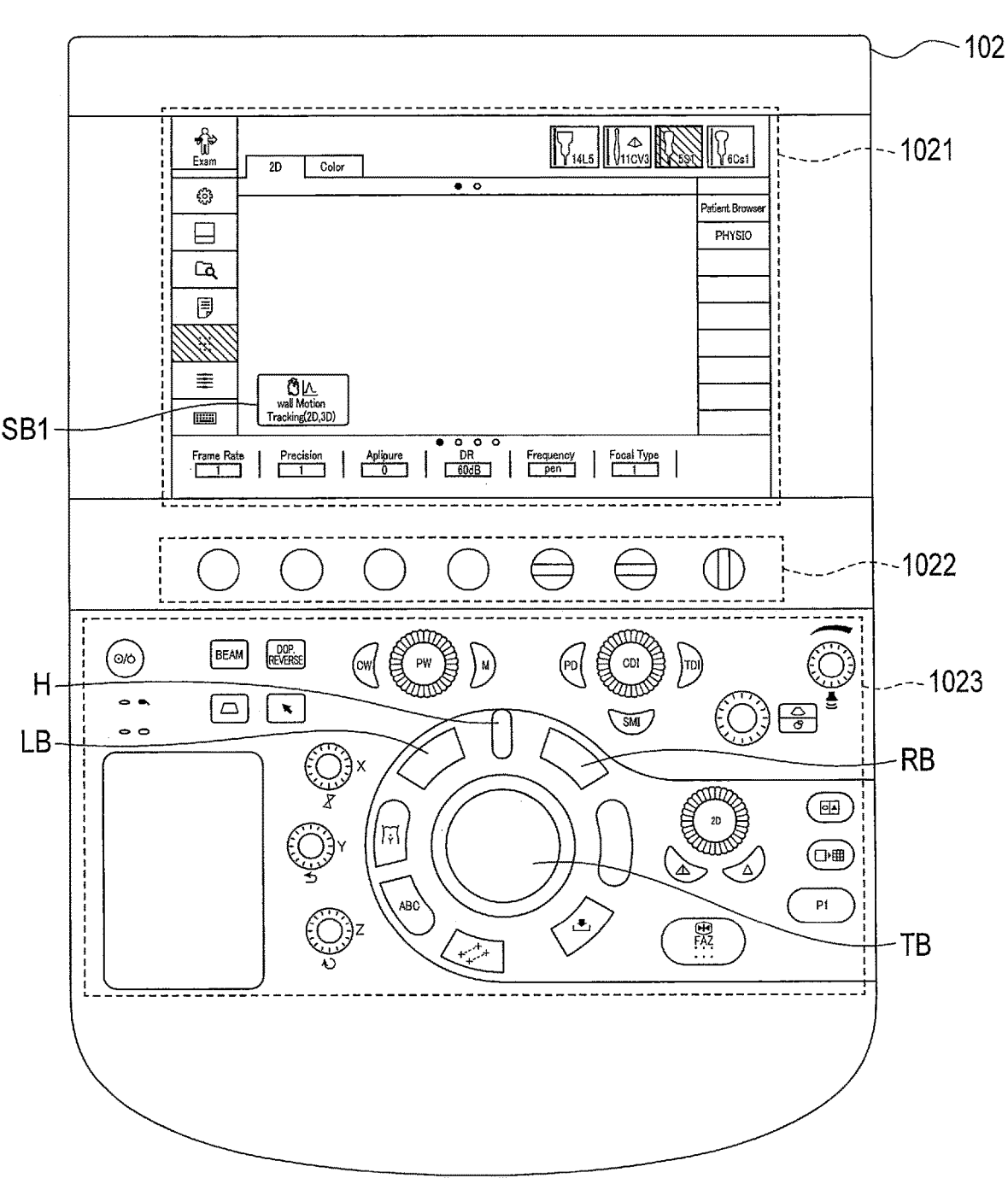
FIG. 3 is an external top view of an input device connected to the ultrasonic diagnosis apparatus according to the first embodiment.

FIG. 3 is an external top view of the input device connected to the ultrasonic diagnosis apparatus according to the first embodiment. The input device 102 shown in FIG. 3 includes a touch panel 1021, a first operation unit 1022, and a second operation unit 1023.

For example, a setting screen of the ultrasonic diagnosis apparatus is displayed on the touch panel 1021. The setting screen includes, for example, a software button for switching the connected ultrasonic probe, a software button for starting a predetermined application, and setting items that can be changed in accordance with the operation of the first operation unit 1022.

Specifically, the software button SB1 shown in FIG. 3 is associated with a command for executing an application related to myocardial function analysis (myocardial function analysis application). When a user selects the software button SB1, the ultrasonic diagnosis apparatus 1 executes the myocardial function analysis application.

The first operation unit 1022 is configured by, for example, a dial knob, a vertically movable switch, and a horizontally movable switch. The first operation unit 1022 is used, for example, when changing the setting items displayed on the screen of the touch panel 1021.

The second operation unit 1023 is configured by, for example, a dial ring, a hardware button, a wheel, and a trackball. The second operation unit 1023 is used, for example, when setting the parameters of the processing of setting the contour of a structure (contour-setting processing) in the myocardial function analysis application.

Specifically, the second operation unit 1023 includes a left button LB and a right button RB corresponding to hardware buttons, a wheel H, and a trackball TB. For example, the user moves the pointer displayed on the display using the trackball TB. The user also performs various operations on the application using the left button LB, the right button RB, and the wheel H.

The communication interface 170 is connected to the external device 104 via, for example, the network NW, and performs data communication with the external device 104.

For example, the processing circuitry 180 functions as the center of the ultrasonic diagnosis apparatus 1. The processing circuitry 180 executes a program stored in the internal storage circuitry 130, thereby implementing a function corresponding to the program. The processing circuitry 180 includes, for example, a B-mode processing function 181, a Doppler processing function 182, an image generation function 183, an acquisition function 184 (acquisition unit), a contour-estimation function 185 (contour-estimation unit), a contour-correction function 186 (contour-correction unit), a display control function 187 (display controller), and a system control function 188 (controller).

The B-mode processing function 181 is a function of generating B-mode data based on the reception signals (echo signals) received from the ultrasound reception circuitry 120. In the B-mode processing function 181, the processing circuitry 180, for example, performs an envelope detection process, a logarithmic compression process, and the like on the reception signals received from the ultrasound reception circuitry 120 to generate data (B-mode data) that expresses the signal intensity of the reception signals (echo reflection intensity) with a value of brightness (brightness value). The generated B-mode data is stored in a RAW data memory (not shown) as B-mode raw data on two-dimensional ultrasound scan lines (rasters).

The processing circuitry 180 can also perform harmonic imaging through the B-mode processing function 181. The harmonic imaging is an imaging method that utilizes not only a fundamental wave component but also a harmonic wave component (harmonic component) included in the reflection wave signals of the ultrasonic waves. The harmonic imaging includes, for example, a tissue harmonic imaging (THI) not using a contrast agent and a contrast harmonic imaging (CHI) using a contrast agent. In the THI, a harmonic component can be extracted using an amplitude modulation (AM) method, a phase modulation (PM) method, or an imaging method called an AMPM method, which is a combination of the AM method and the PM method.

In the AM method, the PM method, and the AMPM method, ultrasound transmission is performed more than once for a single scanning line, with different amplitudes and/or phases. Through the above processing, the ultrasound reception circuitry 120 generates a plurality of reflection wave data at each scanning line, and outputs the generated reflection wave data. With the B-mode processing function 181, the processing circuitry 180 performs addition-subtraction processing on the plurality of reflection wave data at the respective scanning lines in accordance with a modulation method, and thereby extracts a harmonic component. Then, the processing circuitry 180 performs envelope detection processing or the like on the reflection wave data of the harmonic component and thereby generates B-mode data.

In the CHI, a harmonic component is extracted using, for example, a frequency filter. With the B-mode processing function 181, the processing circuitry 180 can separate reflection wave data (a harmonic component) whose reflection source is the contrast agent and reflection wave data (a fundamental wave component) whose reflection source is the tissue in the living body P. Thus, the processing circuitry 180 can select a harmonic component from a contrast agent using a filter and generate B-mode data for generating contrast image data.

The B-mode data for generating contrast image data is data expressing, with a brightness value, an echo reflection intensity of the wave whose reflection source is the contrast agent. The processing circuitry 180 can also extract a fundamental wave component from the reflection wave data of the living body P and generate B-mode data for generating living tissue image data.

The Doppler processing function 182 is a function of analyzing the frequency of the reception signals received from the ultrasound reception circuitry 120 and thereby generating data (Doppler information) obtained by extracting motion information based on the Doppler effect of a moving object in a region of interest (ROI) set in the scan area. The generated Doppler information is stored in a raw data memory (not shown) as Doppler raw data (also referred to as "Doppler data") on the two-dimensional ultrasonic scanning lines.

Specifically, with the Doppler processing function 182, the processing circuitry 180 estimates an average velocity, an average dispersion value, an average power value, etc., for example, as motion information of a moving object at each sampling point, and generates Doppler data indicating the estimated motion information. The moving object here is, for example, a blood flow, tissue portions such as the cardiac wall, a contrast medium, etc. With the Doppler processing function 182, the processing circuitry 180 according to the present embodiment estimates an average bloodstream velocity, a dispersion value of a bloodstream velocity, a power value of a bloodstream signal, etc., as motion information of a bloodstream (bloodstream information) at each sampling point, and generates Doppler data indicating the estimated bloodstream information.

The image generation function 183 is a function of generating B-mode image data based on the data generated by the B-mode processing function 181. With the image generation function 183, the processing circuitry 180, for example, converts (scan-converts) a scanning line signal sequence of an ultrasonic scan into a scanning line signal sequence of a video format representatively used by television, etc. to generate image data for display (display image data). Specifically, the processing circuitry 180 executes a raw-pixel conversion, such as a coordinate conversion corresponding to the mode of the ultrasonic scan by the ultrasonic probe 101, on B-mode raw data stored in the raw data memory to generate two-dimensional B-mode image data (also referred to as "ultrasonic image data") consisting of pixels. In other words, with the image generation function 183, the processing circuitry 180 generates a plurality of ultrasonic images (medical images) respectively corresponding to a plurality of consecutive frames through transmission and reception of ultrasonic waves.

The processing circuitry 180 also executes, for example, a raw-pixel conversion on Doppler raw data stored in the raw data memory to generate Doppler image data that visualizes bloodstream information. The Doppler image data is average velocity image data, dispersion image data, power image data, or image data of a combination thereof. The processing circuitry 180 generates, as Doppler image data, color Doppler image data that represents the bloodstream information by color and Doppler image data that represents a piece of bloodstream information in a waveform shape with a gray scale.

The acquisition function 184 is a function of acquiring command information input by a user. The command information is, for example, a command for executing the application or the function and a command for selecting an arbitrary item. For example, with the acquisition function 184, the processing circuitry 180 receives a desired correction mode among the multiple correction modes for correcting the contour input by the user. The processing circuitry 180 receives information on the cross section of a structure input by the user.

The contour-estimation function 185 is a function of estimating the contour of the structure. For example, with the contour-estimation function 185, the processing circuitry 180 estimates a contour of a desired structure based on a medical image. Specifically, the processing circuitry 180 estimates the contour of the structure included in the medical image data by applying a trained model to the medical image data. The trained model is, for example, a prepared machine training model trained based on ultrasonic image data including an examination target.

The processing circuitry 180 may estimate the contour of the structure based further on the information on the cross section of the structure. The information on the cross section of the structure is, for example, data in the form of a one-hot vector representing, by "0" or "1", the presence or absence of an element corresponding to the type of the cross section of the structure. For the trained model, each model corresponding to the information on the cross section of the structure may be prepared, or a single model may be prepared irrespective of the information on the cross section of the structure.

In the present embodiment, the medical image is an ultrasonic image acquired by the ultrasonic probe 101. The structure is, for example, a cardiac muscle. When the structure is a cardiac muscle, the information on the cross section of the structure is information on a reference cross-sectional image of the heart. The reference cross-sectional image is, for example, an apical two chamber view (Apical-2Ch: A2C), an apical three chamber view (Apical-3Ch: A3C), and an apical four chamber view (Apical-4Ch: A4C). In the ultrasonic image, all of A2C, A3C, and A4C have the cardiac apex positioned in the upper part of the image.

Also, in the present embodiment, the contour of the structure corresponds to the cardiac muscle related to the left ventricle. In this instance, the contour of the cardiac muscle includes a first contour line corresponding to the endocardium of the left ventricle and a second contour line set on the outer side of the first contour line. Also, in the present embodiment, each of the first contour line and the second contour line is, for example, an open curve having a projecting shape on the cardiac apex side.

The machine training model according to the present embodiment is assumed, typically, to be a deep neural network (DNN), which is a multiple-layer network model simulating neural circuitry of a brain of a living being. The DNN includes a composite function with parameters that are defined by a combination of a plurality of adjustable functions and parameters.

The trained model of the present embodiment correctly estimates the contour based on an ultrasonic image, but the contour estimated is not necessarily optimized as a contour for cardiac muscle evaluation. For example, since the cardiac apex in the ultrasonic image is closest to the body surface, an artifact is likely to be generated due to multiple reflection of ultrasonic beams, resulting in the cardiac apex being shown at a position deeper than the actual position. In addition, since the free wall of the cardiac muscle in the ultrasonic image is often at a position having a large deflection angle of ultrasonic beams, that is, at a position greatly deviating from the center, for example, the ultrasonic beams are likely to drift, resulting in the free wall being shown at a position closer to the inner cavity than the actual position. Furthermore, if the structures in the cardiac chamber are included within the thickness of the ultrasonic beams in the slice direction, for example, the endocardium may be shown on side further inward than the actual position.

The contour-correction function 186 is a function of correcting the estimated contour. For example, with the contour-correction function 186, the processing circuitry 180 corrects the estimated contour according to a desired correction mode. In the present embodiment, the correction mode is a mode for correcting so as to expand a reference contour. The reference contour is, for example, a contour estimated by the contour-estimation function 185. Hereinafter, the state in which no correction is made to the contour will be referred to as "correction mode M0".

For example, if four correction modes, modes 1 to 4, are set, multiple correction amounts and multiple correction modes are pre-stored in the internal storage circuitry 130 such that the correction amounts and the correction modes are associated with each other. The multiple correction modes may be set so that the correction amounts increase as the number allocated to the correction modes increases. The increase in the correction amounts corresponds to the case where the area of the region included in the contour in the N correction mode (e.g., $4 \geq N > 0$) becomes larger than the area of the region included in the contour in the N–1 correction mode.

The display control function 187 is a function of causing a display as the output device 103 to display an image based on various kinds of ultrasonic image data generated by the image generation function 183. Specifically, with the display control function 187, the processing circuitry 180, for example, controls the displaying, on the display, of an image based on the B-mode image data, the Doppler image data, or the image data including both of these types of data, generated by the image generation function 183. The processing circuitry 180 may display the contour of the structure on the ultrasonic image.

More specifically, with the display control function 187, the processing circuitry 180 converts (scan-converts) a scanning line signal sequence of an ultrasonic scan into a scanning line signal sequence of a video format representatively used by television, etc., to generate display image data. The processing circuitry 180 may also perform various types of processing, such as dynamic range, brightness, contrast, $\gamma$ curve corrections, and an RGB conversion, on the display image data. The processing circuitry 180 may also add supplementary information, such as textual information, a scale, and a body mark of various parameters, to the display image data. The processing circuitry 180 may also generate a user interface (graphical user interface (GUI)) to allow the operator to input various commands through the input device, and cause the display to display the GUI.

The system control function 188 is a function of integrally controlling the overall operations of the ultrasonic diagnosis apparatus 1. For example, with the system control function 188, the processing circuitry 180 controls the ultrasound transmission circuitry 110 and the ultrasound reception circuitry 120 based on a parameter related to transmission and reception of ultrasonic waves.

Also, with the system control function 188, the processing circuitry 180, for example, may store in the internal storage circuitry 130 the parameters set or changed during execution of the programs. Specifically, the processing circuitry 180 stores the information on the cross section received by the acquisition function 184 and the correction modes in the internal storage circuitry 130 in a manner to associate them with each other.

The above descriptions focus on the configuration of the ultrasonic diagnosis apparatus of the first embodiment. Next, the operation of the contour-setting processing according to the first embodiment will be described. The contour-setting processing according to the first embodiment includes processing of automatically estimating the contour (automatic-contour-estimation processing) and processing of correcting the automatically estimated contour (contour-correction processing).

FIG. 4 is a flowchart for explaining operations of the processing circuitry that executes the contour-setting processing according to the first embodiment. The contour-setting processing shown in FIG. 4 is started, for example, when a user executes the myocardial function analysis application.

Step ST110

When the myocardial function analysis application is executed, the processing circuitry 180 executes the acquisition function 184. When the processing circuitry 180 executes the acquisition function 184, the processing circuitry 180 receives selection of a cross section. At this time, the user selects a cross section that matches an ultrasonic image displayed on a display.

Step ST120

After receiving selection of a cross section, the processing circuitry 180 receives execution of automatic tracing through its acquisition function 184. At this time, the user selects a software button associated with execution of the automatic tracing (automatic-contour-estimation processing).

A specific example of the user operations of steps ST110 through ST120 will be described below with reference to FIG. 5 through FIG. 9.

Figure 5:
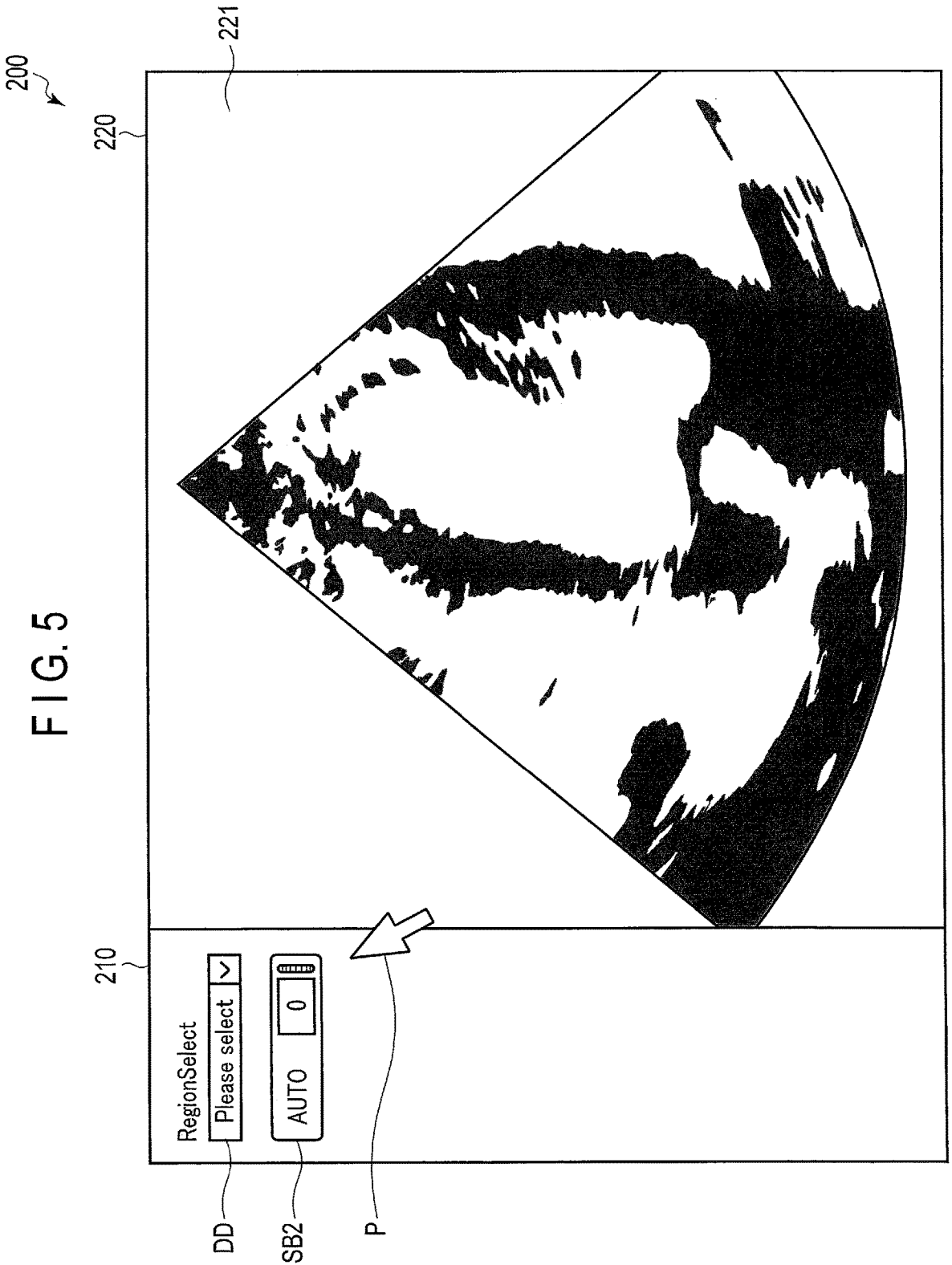
FIG. 5 is a diagram showing an example of a display screen prior to execution of automatic-contour-estimation processing according to the first embodiment.
Figure 6:
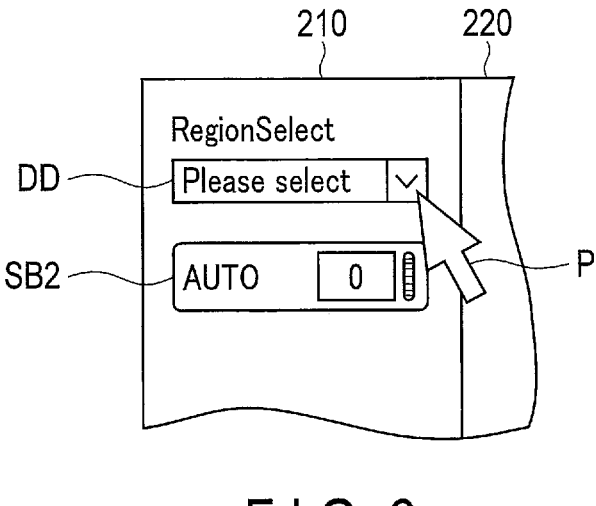
FIG. 6 is a diagram for explaining parameter setting of the automatic-contour-estimation processing according to the first embodiment.
Figure 7:
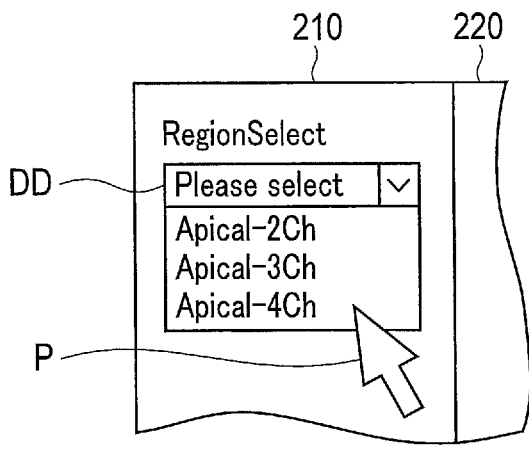
FIG. 7 is a diagram for explaining parameter setting of the automatic-contour-estimation processing according to the first embodiment.
Figure 8:
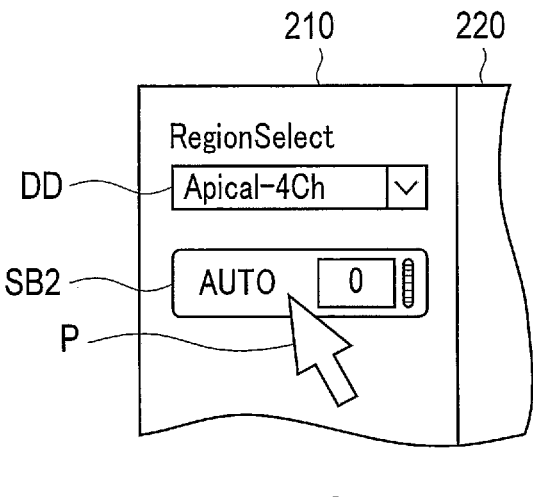
FIG. 8 is a diagram for explaining parameter setting of the automatic-contour-estimation processing according to the first embodiment.

FIG. 5 is a diagram showing an example of a display screen prior to execution of the automatic-contour-estimation processing according to the first embodiment. The display screen 200 shown in FIG. 5 includes a parameter setting region 210 and an image display region 220. A drop down DD and a software button SB2 are displayed on the parameter setting region 210. An ultrasonic image 221 is displayed on the image display region 220. For example, an apical four chamber view is shown in the ultrasonic image 221. The user can move the pointer P displayed on the display screen 200 by, for example, operating the trackball TB. Also, the user can select a software button or the like indicated by the pointer P by, for example, operating the left button LB, the right button RB, and the wheel H.

FIG. 6 through FIG. 9 are diagrams for explaining the parameter setting of the automatic-contour-estimation processing according to the first embodiment. FIG. 6 through FIG. 9 show a part of the display screen 200. The user moves the pointer P and clicks the drop-down DD to thereby display a drop-down list showing multiple items. The drop-down list shows, for example, Apical-2Ch, Apical-3Ch, and Apical-4Ch, which are items of a reference cross section. The user selects the item "Apical-4Ch" corresponding to the apical four chamber view shown in the ultrasonic image 221. The user selects the software button SB2 in the state where the item "Apical-4Ch" is selected. Through this operation, the automatic-contour-estimation processing is executed.

Figure 9:
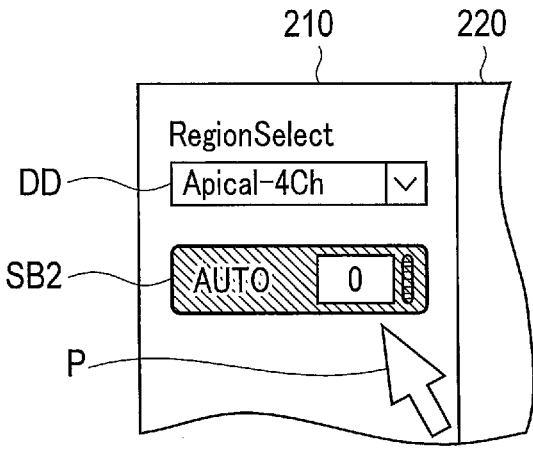
FIG. 9 is a diagram for explaining parameter setting of the automatic-contour-estimation processing according to the first embodiment.

When the automatic-contour-estimation processing is executed, the software button SB2 is highlighted on the display, as shown in FIG. 9. The numerical value shown on the software button SB2 corresponds to the correction mode. FIG. 9 shows a numerical value "0" indicating the correction mode M0.

Step ST130

After receiving execution of automatic tracing, the processing circuitry 180 executes the contour-estimation function 185. When the processing circuitry 180 executes the contour-estimation function 185, the processing circuitry 180 estimates the contour of the structure based on the ultrasonic image. At this time, the processing circuitry 180 may estimate the contour of the structure based on the information on the selected cross section.

Step ST140

After estimating the contour of the structure, the processing circuitry 180 displays the estimated contour on the ultrasonic image by implementing the display control function 187.

Figure 10:
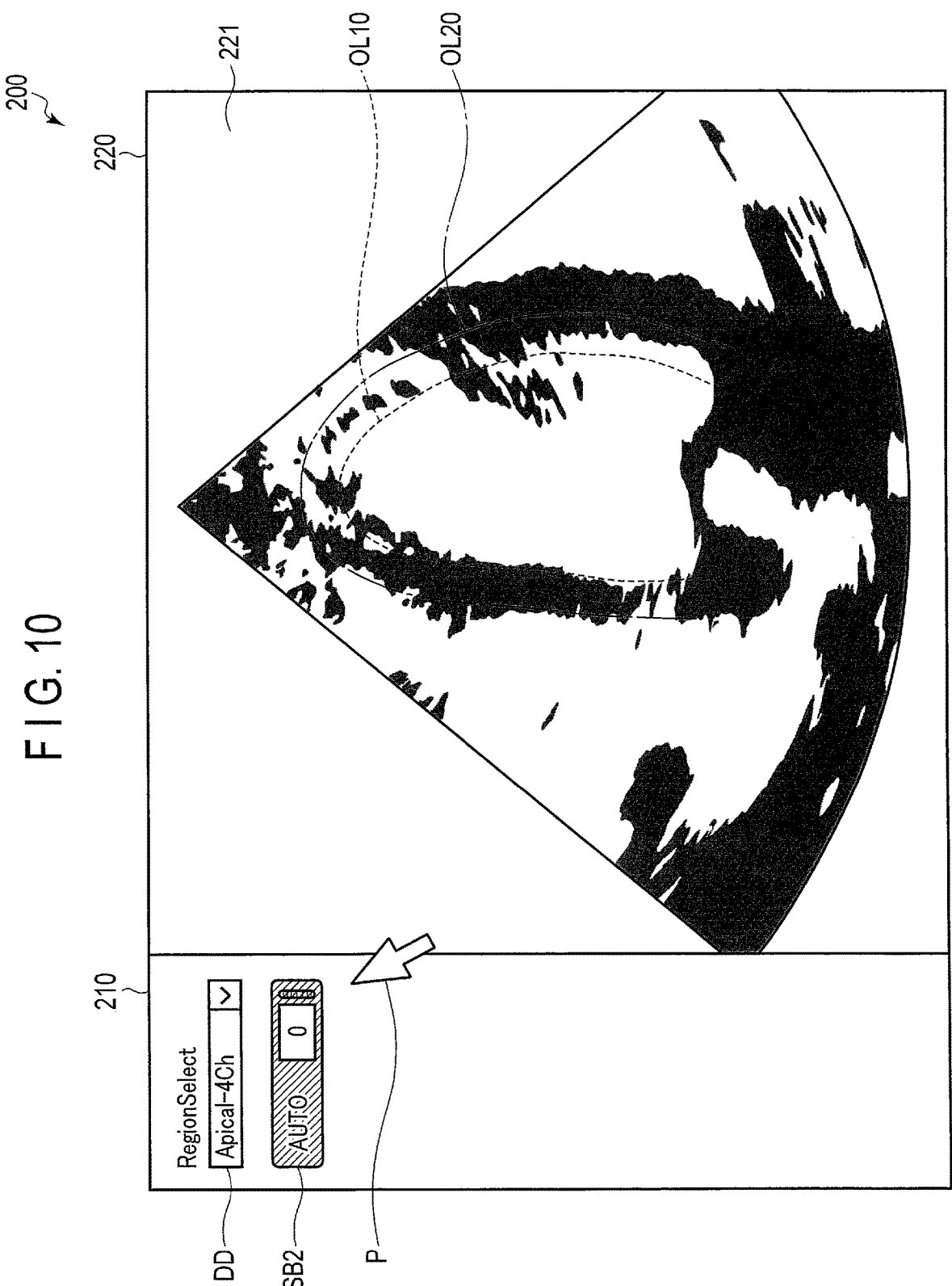
FIG. 10 is a diagram showing an example of a display screen posterior to execution of the automatic-contour-estimation processing according to the first embodiment.

FIG. 10 is a diagram showing an example of a display screen posterior to execution of the automatic-contour-estimation processing according to the first embodiment. FIG. 10 shows estimated contours, a first contour line OL10 and a second contour line OL20, that are displayed on the ultrasonic image 221 when the item "Apical-4Ch" is selected and the automatic-contour-estimation processing is performed. The first contour line OL10 corresponds to the endocardium of the left ventricle of the heart. The second contour line OL20 is set outside the first contour line OL10 at a predetermined distance from the first contour line OL10. Both the first contour line OL10 and the second contour line OL20 are open curves having a projecting shape on the cardiac apex side. Thus, the region surrounded by the first contour line OL10 and the second contour line OL20 corresponds to the cardiac muscle related to the left ventricle.

Step ST150

After displaying the estimated contour on the ultrasonic image, the processing circuitry 180 receives selection of a correction mode through its acquisition function 184. At this time, the user selects a desired correction mode among the multiple correction modes by performing an arbitrary operation on the software button SB2 highlighted on the display.

FIG. 11 is a diagram for explaining transition of the multiple correction modes according to the first embodiment. FIG. 11 shows a list of five correction modes M0 through M4 corresponding to different numerical values shown on the software button SB2. It is possible to transition between these five correction modes M0 though M4 through the user operation. The transition between the correction modes may be in ascending order (e.g., 0→1→2→3→4→0→1 . . . ) or descending order (e.g., 4→3→2→1→0→4→ . . . ). Hereinafter, the operation of transition in ascending order will be referred to as an "ascending operation", and the operation of transition in descending order will be referred to as a "descending operation".

FIG. 12 is a diagram for explaining a method of switching the correction modes according to the first embodiment. In step ST210, the user moves the pointer P onto a software button in the correction mode M1. Next, the user performs step ST220*a* in the ascending operation, and performs step ST220*b* in the descending operation.

In step ST220*a*, the user clicks the left button LB (left-button click), or scrolls the wheel H upward (upward scroll). Through the operation of step ST220*a*, the correction mode will be the correction mode M2 in step ST230*a* and the contour-correction processing will be simultaneously performed.

On the other hand, in step ST220*b*, the user clicks the right button RB (right-button click), or scrolls the wheel H downward (downward scroll). Through the operation of step ST220*b*, the correction mode will be the correction mode M0 in step ST230*b* and the contour-correction processing will be simultaneously performed.

Step ST160

After receiving selection of a correction mode, the processing circuitry 180 implements the contour-correction function 186. When the processing circuitry 180 implements the contour-correction function 186, the processing circuitry 180 corrects the contour according to the selected correction mode. Specifically, the processing circuitry 180, for example, corrects the contour according to the correction mode by using a table associating the correction modes, the directions, and the correction amounts with one another. In the present embodiment, at least a part of the contour is changed every time the correction mode is switched. Description below will focus on expanding the contour through the ascending operation.

Figure 13:
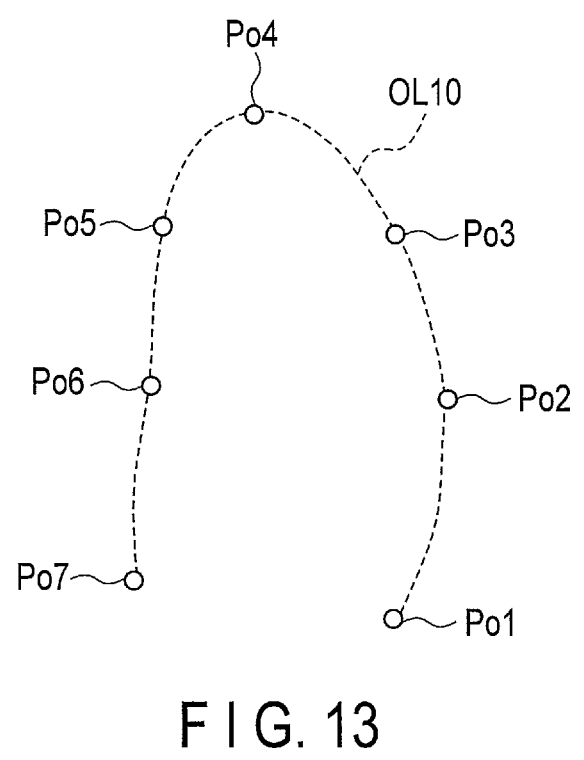

FIG. 13 is a diagram for explaining multiple points defining the contour according to the first embodiment. The first contour line OL10 shown in FIG. 13 seamlessly connects, for example, seven points Po1 through Po7. That is, the movement of any of these points corresponds to a change in the shape of the contour. Hereinafter, the correction of the contour will be described in association with the movement of the seven points Po1 through Po7. Since the second contour line OL20 may be handled in the same manner as the first contour line OL10, description of the second contour line OL20 will be omitted.

FIG. 14 is a diagram showing an example of a table associating the correction modes, the directions, and the correction amounts with one another according to the first embodiment. The table 300 shown in FIG. 14 associates the correction modes, the directions, and the correction amounts of the case where A4C is set as a cross section. For example, the correction mode M1 associates a direction "upward" with a correction amount "3", so that the contour in the correction mode M0 is expanded in the upward direction by a correction amount of "3". The correction mode M2 associates a direction "right" with a correction amount "3", so that the contour in the correction mode M1 is expanded in the right direction by a correction amount of "3". The correction mode M3 associates a direction "upward" with a correction amount "3", so that the contour in the correction mode M2 is expanded in the upward direction by a correction amount of "3". The correction mode M4 associates a direction "right" with a correction amount "3", so that the contour in the correction mode M3 is expanded in the right direction by a correction amount of "3".

For example, the "direction" in the table 300 corresponds to any of the seven points Po1 through Po7 shown in FIG. 13. For example, the direction "upward" corresponds to the point Po4, the direction "right" corresponds to the three points Po1 through Po3, and the direction "left" corresponds to the three points Po5 through Po7. These directions may be associated with a clinical site. For example, since the table 300 sets A4C as the cross section, the direction "upward" may be associated with the cardiac apex side, the direction "right" may be associated with the free wall (or side wall) side, and the direction "left" may be associated with the septal side.

When A2C is set as the cross section, the direction "upward" may be associated with the cardiac apex side, the direction "right" may be associated with the anterior wall side, and the direction "left" may be associated with the inferior wall side. When A3C is set as the cross section, the direction "upward" may be associated with the cardiac apex side, the direction "right" may be associated with the septal side, and the direction "left" may be associated with the inferior wall side.

FIG. 15 is a diagram for showing an example of a table associating the directions, the points, and the correction amounts in the correction mode M1 in the table shown in FIG. 14. The table 310 shown in FIG. 15 associates the directions, the points, and the correction amounts in the correction mode M1. Since the correction mode M1 associates a direction "upward" with a correction amount "3", the point Po4 corresponding to the upward direction is expanded by a correction amount of "3".

FIG. 16 is a diagram for showing an example of a table associating the directions, the points, and the correction amounts in the correction mode M2 in the table shown in FIG. 14. The table 320 shown in FIG. 16 associates the directions, the points, and the correction amounts in the correction mode M2. Since the correction mode M2 associates a direction "right" with a correction amount "3", each of the three points Po1 through Po3 corresponding to the right direction is expanded by a correction amount of "3".

FIG. 17 is a diagram for explaining transition of multiple corrected contours corresponding to the multiple correction modes according to the first embodiment. FIG. 17 shows five ultrasonic images 222A through 222E, which correspond to the five correction modes M0 through M4, respectively. The direction indicated by the arrow on the ultrasonic image corresponds to the direction in the table 300 shown in FIG. 14.

Specifically, the upward direction of the contour in the correction mode M0 is corrected in the correction mode M1; the right direction of the contour in the correction mode M1 is corrected in the correction mode M2; the upward direction of the contour in the correction mode M2 is corrected in the correction mode M3; and the right direction of the contour in the correction mode M3 is corrected in the correction mode M4. The correction amount of the first contour line and the correction amount of the second contour line are equal to each other. That is, the distance between the first contour line and the second contour line is the same throughout the five correction modes M0 through M4.

In the above instance, the directions and the correction amounts of the correction mode mainly match each other. In the table 320 shown in FIG. 16, for example, the directions and the correction amounts match each other. However, the directions and the correction amounts of the correction mode need not necessarily match each other. This will be described with reference to FIG. 18 below.

FIG. 18 is a diagram showing another example of the table shown in FIG. 16. The table 320A shown in FIG. 18 associates the directions, the points, and the correction amounts in the correction mode M2. In the table 300 shown in FIG. 14, the correction mode M2 associates a direction "right" and a correction amount "3"; however, in the table 320A, the point Po1 is set to a correction amount "1", and the point Po2 and the point Po3 are set to a correction amount "3".

In sum, the correction amounts of the multiple correction modes are set according to the information on the cross section (e.g., a reference cross-sectional image of the heart). The correction amounts of the multiple correction modes are set so as to expand the estimated contour. The correction amount of each of the multiple correction modes is set so as to increase as the number allocated to each of the correction modes increases. The correction amounts of the multiple correction modes are equal to each other irrespective of the direction. The correction amounts related to the first contour line of the multiple correction modes are equal to the correction amounts related to the second contour line of the multiple correction modes.

The correction amounts of the multiple correction modes may vary depending on the direction. The table 300A shown in FIG. 19, for example, is another example of the table shown in FIG. 14. The table 300 shown in FIG. 14 sets the correction amount to "3" irrespective of the direction; however, the table 300A sets the correction amount to "5" when the direction is "upward", and sets the correction amount to "3" when the direction is "right". When the direction "upward" is associated with the cardiac apex side, for example, the multiple correction modes are set so that the correction amount on the cardiac apex side of the left ventricle is larger than the other correction amounts.

The correction amounts related to the first contour line of the multiple correction modes may differ at least partially from the correction amounts related to the second contour line of the multiple correction modes. For example, the table 300B shown in FIG. 20 associates the correction modes, the directions, the correction amounts on the inner side (first contour line) and the correction amounts on the outer side (second contour line). The table 300B sets the correction amount on the inner side to "3" and sets the correction amount on the outer side to "4".

Step ST170

After correcting the contour, the processing circuitry 180 displays the corrected contour on the ultrasonic image through its display control function 187.

Figure 21:
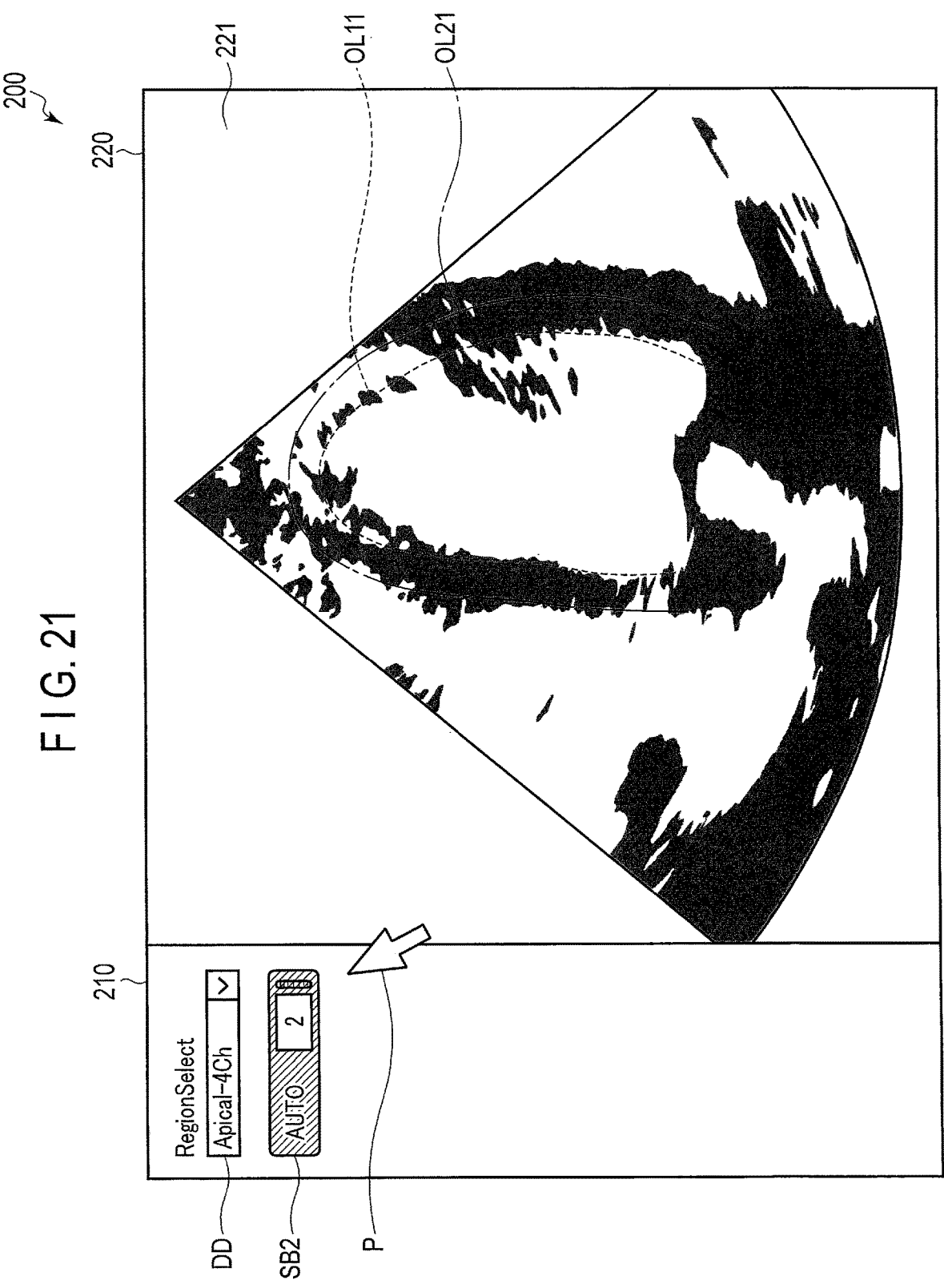
FIG. 21 is a diagram showing an example of a display screen posterior to execution of contour-correction processing according to the first embodiment.

FIG. 21 is a diagram showing an example of a display screen posterior to execution of the contour-correction processing according to the first embodiment. In FIG. 21, with the correction mode M2 set, a first contour line OL11 and a second contour line OL21 corresponding to the correction mode M2 are shown on the ultrasonic image 221. The first contour line OL11 and the second contour line OL21 are, for example, contour lines obtained by correcting the first contour line OL10 and the second contour line OL20 based the table 300 shown in FIG. 14.

Step ST180

After displaying the corrected contour on the ultrasonic image, the processing circuitry 180 implements its system control function 188 to store the selected cross section and the selected correction mode in the internal storage circuitry 130 in a manner to associate them with each other. After step ST180, the contour-setting processing is completed.

FIG. 22 is a diagram showing an example of a table associating the cross sections and the correction modes with each other according to the first embodiment. The table 400 shown in FIG. 22 associates the cross sections and the correction modes. The table 400 stores the cross sections and the correction modes selected by the user. For example, after estimating the contour through automatic tracing, the processing circuitry 180 may select a correction mode stored in association with a set cross section by referring to the table 400 and display the corrected contour on the ultrasonic image.

As described above, the ultrasonic diagnosis apparatus according to the first embodiment acquires an ultrasonic image using a probe, estimates the contour of a desired structure based on the ultrasonic image, receives a desired correction mode among multiple correction modes for correcting the estimated contour, and corrects the estimated contour according to the desired correction mode.

Since the ultrasonic diagnosis apparatus according to the first embodiment need not manually set an estimated contour from scratch, the operation performed until a contour desired by the user is set will be easy.

First Application Example of First Embodiment

In the first embodiment, the operation of displaying a single ultrasonic image in an image display region and performing the contour-setting processing is described; however, the embodiment is not limited thereto. In a first application example of the first embodiment, a plurality of ultrasonic images may be displayed in an image display region to perform contour-setting processing.

Figure 23:
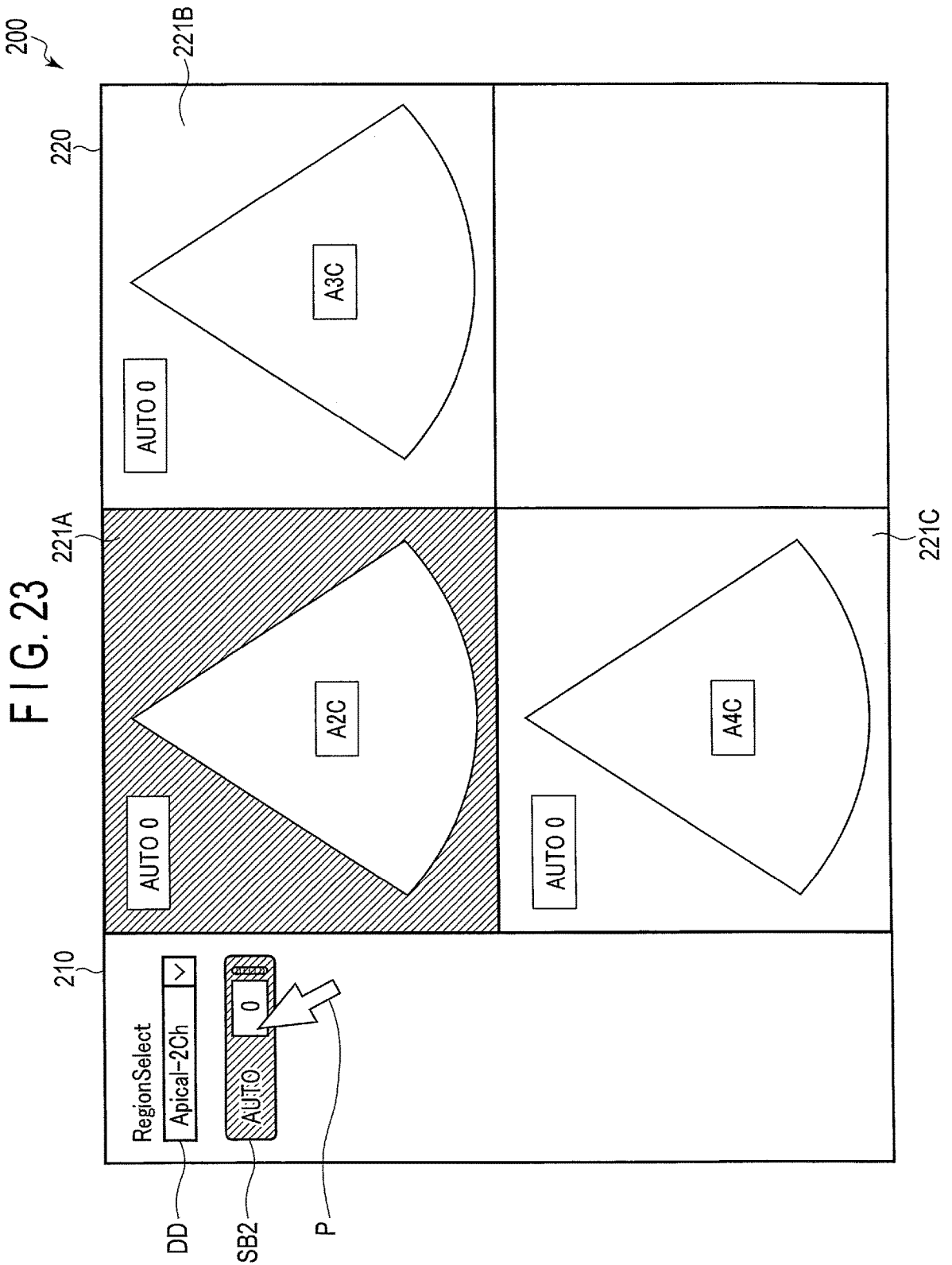
FIG. 23 is a diagram showing an example of a display screen prior to execution of contour-correction processing according to a first application example of the first embodiment.

FIG. 23 is a diagram showing an example of a display screen prior to execution of the contour-correction processing according to the first application example of the first embodiment. A first ultrasonic image 221A, a second ultrasonic image 221B, and a third ultrasonic image 221C are displayed in the image display region 220 shown in FIG. 23. The first ultrasonic image 221A is a cross-sectional image of A2C, the second ultrasonic image 221B is a cross-sectional image of A3C, and the third ultrasonic image 221C is a cross-sectional image of A4C. The first ultrasonic image 221A, the second ultrasonic image 221B, and the third ultrasonic image 221C are, for example, cross-sectional images generated from the same volume data.

In FIG. 23, with the item "Apical-2Ch" selected and the automatic-contour-estimation processing performed, an automatically estimated contour is displayed on each of the ultrasonic images, and a character "AUTO 0" indicating that a contour has been automatically estimated is displayed. After the state shown in FIG. 23, that is, the state in the correction mode M0, the user sets the correction mode M2 by performing the contour-correction processing.

FIG. 24 is a diagram showing an example of a display screen posterior to execution of the contour-correction processing according to the first application example of the first embodiment. In FIG. 24, with the correction mode M2 set for the item "Apical-2Ch", a character "AUTO 2" indicating the correction mode M2 is displayed on the first ultrasonic image 221A. At this time, the ultrasonic diagnosis apparatus 1 also applies the correction mode M2 to the contours displayed on the second ultrasonic image 221B and the third ultrasonic image 221C. Since this allows the user to set a mode only for a single ultrasonic image when displaying multiple ultrasonic images and performing the contour-correction processing, the operation performed until a contour desired by the user is set will become easy. That is, when contours of multiple cross-sectional images are to be corrected, a correction mode of a contour of another cross-sectional image may be set according to the correction mode received for a single cross-sectional image.

In this instance, a correction amount of a correction mode applied to the contours displayed on the second ultrasonic image 221B and the third ultrasonic image 221C when the correction mode M2 is selected on the first ultrasonic image 221A, may be set according to the correction amount of the correction mode selected on the first ultrasonic image 221A. That is, when contours of multiple cross-sectional images are to be corrected, a correction amount of another cross-sectional image may be set according to a correction amount of a single cross-sectional image.

Second Application Example of First Embodiment

In the first embodiment, setting of a correction amount to expand an estimated contour is described; however, the embodiment is not limited thereto. In a second application example of the first embodiment, a correction amount may be set to narrow an estimated contour. For example, in the field of gynecology, when a contour of a fetus is to be automatically estimated, the placenta outside the actual contour of the fetus may be falsely recognized and estimated as the contour of the fetus. In this case, correcting an automatically estimated contour to reduce its size can be considered.

FIG. 25 is a diagram showing an example of a table associating the correction modes, the directions, and the correction amounts with one another according to the second application example of the first embodiment. The table 300C shown in FIG. 25 associates the correction modes, the directions, and the correction amounts of the case where a contour of a fetus is extracted. For example, the correction mode M1 associates a direction "inward" with a correction amount "−3", so that the contour in the correction mode M0 is narrowed inward by a correction amount of "−3". The same applies to the other correction modes M2 to M4. That is, the multiple correction modes are set so that the correction amounts decrease as the number allocated to the correction modes increases. The decrease in the correction amounts corresponds to the case where the area of the region included in the contour in the N correction mode becomes smaller than the area of the region included in the contour in the N+1 correction mode. Thus, similar advantageous effects to those of the first embodiment can be expected.

Third Application Example of First Embodiment

In the first embodiment, estimation and correction of the contour of the cardiac muscle is described as a specific example; however, the embodiment is not limited thereto. For example, the ultrasonic diagnosis apparatus 1 according to the first embodiment may estimate and correct the contour of another site such as the prostate gland. The information on the corrected contour may be used for position adjustment made by other medical imaging apparatuses. Other medical imaging apparatuses are, for example, a computed tomography (CT) apparatus and a magnetic resonance imaging (MRI) apparatus.

Second Embodiment

In the first embodiment, the correction amount for correcting the automatically estimated contour is determined in advance and associated with the correction mode. On the other hand, in the second embodiment, calculating the aforementioned correction amount and associating it with the correction mode will be described.

FIG. 26 is a block diagram showing a configuration example of an ultrasonic diagnosis apparatus according to the second embodiment. An ultrasonic diagnosis apparatus 1A shown in FIG. 26 includes an apparatus main body 100A and an ultrasonic probe 101. The apparatus main body 100A is connected to an input device 102 and an output device 103. The apparatus main body 100A is also connected to an external device 104 via a network NW. The external device 104 is, for example, a server equipped with PACS.

The apparatus main body 100A generates an ultrasonic image based on a reflection wave signal received by the ultrasonic probe 101. The apparatus main body 100A includes ultrasound transmission circuitry 110, ultrasound reception circuitry 120, internal storage circuitry 130, an image memory 140, an input interface 150, an output interface 160, a communication interface 170, and processing circuitry 180A.

For example, the processing circuitry 180A is a processor that functions as the center of the ultrasonic diagnosis apparatus 1A. The processing circuitry 180A implements the programs stored in the internal storage circuitry 130 and thereby fulfills the functions corresponding to the programs. The processing circuitry 180A includes, for example, a B-mode processing function 181, a Doppler processing function 182, an image generation function 183, an acquisition function 184 (acquisition unit), a contour-estimation function 185 (contour-estimation unit), a contour-correction function 186 (contour-correction unit), a display control function 187 (display controller), a system control function 188 (controller), and a correction-amount calculation function 189 (correction-amount calculation unit).

The correction-amount calculation function 189 is a function of calculating a correction amount. For example, with the correction-amount calculation function 189, the processing circuitry 180A calculates a correction amount for correcting an estimated contour. Specifically, the processing circuitry 180A calculates multiple correction amounts by comparing an acquired medical image and a reference image.

With the system control function 188 according to the second embodiment, the processing circuitry 180A stores the calculated multiple correction amounts and multiple correction modes in a manner to associate them with each other. At this time, the processing circuitry 180A may update the already-set correction amounts to the calculated correction amounts or store the calculated correction amounts while storing the already-set correction amounts (default correction amounts) in a manner to associate them with each other.

A configuration of the ultrasonic diagnosis apparatus of the second embodiment has been described. Next, the operation of the contour-setting processing according to the second embodiment will be described. The contour-setting processing of the second embodiment includes automatic-contour-estimation processing and contour-correction processing, and further includes processing of calculating a correction amount based on an ultrasonic image (correction-amount-calculation processing).

Figure 27:
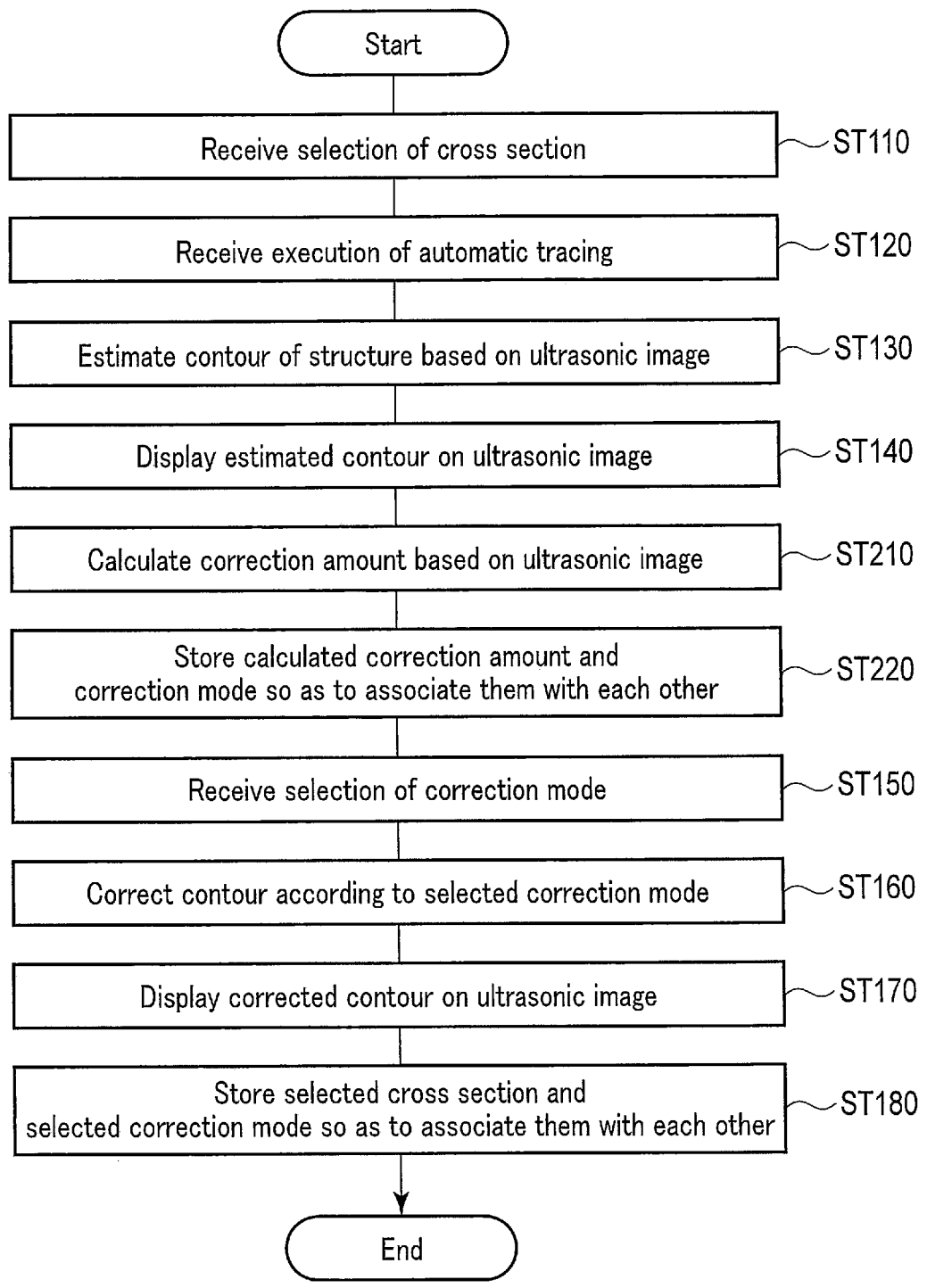
FIG. 27 is a flowchart for explaining operations of processing circuitry that executes contour-setting processing according to the second embodiment.

FIG. 27 is a flowchart for explaining operations of the processing circuitry that executes the contour-setting processing according to the second embodiment. The contour-setting processing shown in FIG. 27 is started, for example, when a user executes a myocardial function analysis application.

The flowchart shown in FIG. 27 is a flowchart that additionally includes steps ST210 and ST220 described below between steps ST140 and ST150 in the flowchart shown in FIG. 4. Thus, a description of steps ST110 through ST180 will be omitted.

Step ST210

After displaying an estimated contour on an ultrasonic image in step ST140, the processing circuitry 180A executes the correction-amount calculation function 189. When the processing circuitry 180A executes the correction-amount calculation function 189, the processing circuitry 180A calculates a correction amount based on the ultrasonic image.

Step ST220

After calculating a correction amount, the processing circuitry 180A implements its system control function 188 to store the calculated correction amount and a correction mode in the internal storage circuitry 130 in a manner to associate them with each other. After step ST220, the contour-setting processing transitions to step ST150.

FIG. 28 is a diagram showing another example of the table shown in FIG. 14, in which the correction amounts have been changed through the correction-amount-calculation processing according to the second embodiment. A table 300D shown in FIG. 28 shows that the correction amounts have been changed from a default correction amount "3" to a calculated correction amount "2". The default correction amount may be managed in another table.

FIG. 29 is a diagram showing another example of the table shown in FIG. 28. A table 300E shown in FIG. 29 shows that the calculated correction amount "2" is stored while the default correction amount "3" is stored.

As described above, since a default correction value is stored, even when a user A changes the correction value through the correction-amount-calculation processing, for example, the correction value can be returned to the default correction value when another user B uses the apparatus. The apparatus may also be configured so that the correction value is reset to a default correction value when the apparatus is turned off.

As described above, the ultrasonic diagnosis apparatus according to the second embodiment acquires an ultrasonic image using a probe, estimates the contour of a desired structure based on the ultrasonic image, calculates multiple correction amounts based on a medical image, stores the multiple correction amounts and multiple correction modes for correcting the estimated contour in a manner to associate them with each other, receives a desired correction mode among the multiple correction modes, and corrects the estimated contour according to the desired correction mode.

Thus, for the ultrasonic diagnosis apparatus according to the second embodiment, like the ultrasonic diagnosis apparatus according to the first embodiment, operation is made easy until a contour desired by the user is set.

Third Embodiment

In the first embodiment and the second embodiment, the ultrasonic diagnosis apparatus having multiple functions related to the contour-setting processing is described. On the other hand, in the third embodiment, a medical image processing apparatus having these multiple functions will be described.

FIG. 30 is a block diagram showing a configuration example of the medical image processing apparatus according to the third embodiment. A medical image processing apparatus 500 shown in FIG. 30 is connected to an input device 501 and an output device 502. The medical image processing apparatus 500 is also connected to a medical imaging apparatus 503 via a network NW. The medical imaging apparatus 503 corresponds to, for example, an ultrasonic diagnosis apparatus. The input device 501, which is approximately the same as the input device 102 shown in FIG. 1, typically corresponds to a mouse and a keyboard. The output device 502 is approximately the same as the output device 103 shown in FIG. 1.

The medical image processing apparatus 500 is, for example, a computer capable of executing a myocardial function analysis application. The medical image processing apparatus 500 includes storage circuitry 510, an input interface 520, an output interface 530, a communication interface 540, and processing circuitry 550.

The storage circuitry 510 includes, for example, a processor-readable storage medium, such as a magnetic storage medium, an optical storage medium, or a semiconductor memory. The storage circuitry 510 stores a program related to myocardial function analysis, various data, etc. For example, the programs and various data may be pre-stored in the storage circuitry 510. Alternatively, the programs and various data may be stored and distributed in, for example, a non-transitory storage medium, and read from the non-transitory storage medium and installed in the storage circuitry 510. The internal storage circuitry 130 stores medical image data generated by the medical imaging apparatus 503, etc., in accordance with an operation input via the input interface 150. The storage circuitry 510 can also transfer the stored medical image data to an external device, etc., via the communication interface 540.

The storage circuitry 510 may be a drive or the like which reads and writes various types of information to and from a portable storage medium, such as a CD drive, a DVD drive, and a flash memory. The storage circuitry 510 can also write the stored data onto a portable storage medium to store the data in the external device via the portable storage medium.

The input interface 520 receives various commands from an operator through the input device 501. The input interface 520 is connected to the processing circuitry 550 via a bus, for example, thereby converting an operation command input by the operator, into an electric signal, and outputting the electric signal to the processing circuitry 550. The input interface 520 is not limited to a component that is connected to a physical operation component such as a mouse and keyboard. Examples of the input interface may include a circuit configured to receive an electric signal corresponding to an operation command input from an external input device provided separately from the medical image processing apparatus 500 and to output this electric signal to the processing circuitry 550.

The output interface 530 is an interface for outputting, for example, an electric signal from the processing circuitry 550 to the output device 502. The output interface 530 is connected to the processing circuitry 550 via a bus, for example, and outputs an electric signal from the processing circuitry 550 to the output device 502.

The communication interface 540 is connected to the medical imaging apparatus 503 and the external apparatus via, for example, the network NW, so that data communication is performed between the apparatuses.

For example, the processing circuitry 550 is a processor that functions as the center of the medical image processing apparatus 500. The processing circuitry 550 executes the programs stored in the storage circuitry 510 to thereby fulfill the functions corresponding to the programs. The processing circuitry 550 includes the acquisition function 184 (acquisition unit), contour-estimation function 185 (contour-estimation unit), contour-correction function 186 (contour-correction unit), display control function 187 (display controller), and system control function 188 (system controller) of the first embodiment. The processing circuitry 550 may further include the correction-amount calculation function 189 (correction-amount calculation unit) of the second embodiment. These various functions are approximately the same as those of the first embodiment and the second embodiment, and a description thereof will be omitted.

As described above, the medical image processing apparatus according to the third embodiment estimates the contour of a desired structure based on a medical image, receives a desired correction mode among multiple correction modes for correcting the estimated contour, and corrects the estimated contour according to the desired correction mode.

Thus, advantageous effects similar to those of the first embodiment and the second embodiment can be expected from the medical image processing apparatus according to the third embodiment.

Application Example of Third Embodiment

The medical imaging apparatus 503 is not necessarily an ultrasonic diagnosis apparatus. For example, the medical imaging apparatus 503 may be an X-ray diagnosis apparatus, a CT apparatus, or an MRI apparatus. The medical image is not necessarily an ultrasonic image. The medical image is, for example, an X-ray image, a CT image, or a magnetic resonance (MR) image.

According to at least one embodiment described above, the operation performed until a contour desired by the user is set can be made easy.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

The invention claimed is:

1. A medical image processing apparatus, comprising:
processing circuitry configured to:
estimate a contour of a structure included in a medical image;
receive a selection of one correction mode among multiple correction modes sequentially displayed one by one on a selection screen of a display;
correct the estimated contour according to correction information associated with the selected one correction mode and comprising at least a correction direction and a correction amount; and
cause the corrected contour to be displayed on the medical image,
wherein the structure is a cardiac muscle,
the contour includes a first contour corresponding to an inner side of the cardiac muscle and a second contour corresponding to an outer side of the cardiac muscle, and
correction information associated with a first correction mode among the multiple correction modes and correction information associated with a second correction mode differing from the first correction mode among the multiple correction modes differ from each other in at least one of the correction direction and the correction amount.

2. The medical image processing apparatus according to claim 1, wherein each of the multiple correction modes has the correction amount set so as to expand the estimated contour.

3. The medical image processing apparatus according to claim 1, wherein
the reference cross-sectional image of the heart is an apical two chamber view,
the contour corresponds to a cardiac muscle related to a left ventricle of the heart, and the correction amount is set larger for a free wall side of the left ventricle than for an inferior wall side of the left ventricle.

4. The medical image processing apparatus according to claim 3, wherein the correction amount is set larger for a cardiac apex side of the left ventricle than other correction amounts.

5. The medical image processing apparatus according to claim 1, wherein
the reference cross-sectional image of the heart is an apical three chamber view or an apical four chamber view,
the contour corresponds to a cardiac muscle related to a left ventricle of the heart, and
the correction amount is set larger for a free wall side of the left ventricle than for a septal side of the left ventricle.

6. The medical image processing apparatus according to claim 1, wherein
the contour includes the first contour, which corresponds to an endocardium, and the second contour set on an outer side of the first contour, and
the first contour and the second contour are open curves having a projecting shape on a cardiac apex side.

7. The medical image processing apparatus according to claim 6, wherein each of the multiple correction modes has the correction amount related to the first contour equal to the correction amount related to the second contour.

8. The medical image processing apparatus according to claim 6, wherein each of the multiple correction modes has the correction amount related to the first contour that differs at least partially from the correction amount related to the second contour.

9. The medical image processing apparatus according to claim 1, further comprising an input unit for the selection of the correction mode from among the multiple correction modes,
wherein the processing circuitry is further configured to switch each of the multiple correction modes according to an operation of scrolling a wheel.

10. The medical image processing apparatus according to claim 1, wherein the processing circuitry is further configured to correct the estimated contour according to the correction information associated with the selected one correction mode and comprising a correction position.

11. The medical image processing apparatus according to claim 1, wherein
the multiple correction modes displayed on the selection screen of the display are represented by information comprising a number, and
the processing circuitry is further configured to correct the estimated contour according to the correction amount determined based on a size of the number corresponding to the selected one correction mode.

12. The medical image processing apparatus according to claim 1, wherein
a plurality of the medical images are used, and
the processing circuitry is further configured to select, in response to receiving the selection of the one correction mode for one of the medical images, one or more correction modes for one or more remaining images of the medical images.

13. The medical image processing apparatus according to claim 1, wherein the processing circuitry is further configured to estimate the contour of the structure included in the medical image by applying a trained model to the medical image.

14. An ultrasonic diagnosis apparatus comprising:

the medical image processing apparatus according to claim 1; and a probe configured to acquire an ultrasonic image as the medical image.

15. A medical image processing apparatus, comprising:

processing circuitry configured to estimate a contour of a structure included in a medical image;

receive a selection of one correction mode among multiple correction modes sequentially displayed one by one on a selection screen of a display;

correct the estimated contour according to correction information associated with the selected one correction mode and comprising at least a correction direction and a correction amount; and cause the corrected contour to be displayed on the medical image, wherein a plurality of the medical images are used, and the processing circuitry is further configured to select, in response to receiving the selection of the correction mode for one of the medical images, one or more correction modes for one or more remaining images of the medical images.

16. A non-transitory processor-readable storage medium comprising a program which, when executed by a processor, causes the processor to perform a method, comprising:

estimating a contour of a structure included in a medical image;

receiving a selection of one correction mode among multiple correction modes sequentially displayed one by one on a selection screen of a display;

correcting the estimated contour according to correction information associated with the selected one correction mode and comprising at least a correction direction and a correction amount; and causing the corrected contour to be displayed on the medical image, wherein the structure is a cardiac muscle, the contour includes a first contour corresponding to an inner side of the cardiac muscle and a second contour corresponding to an outer side of the cardiac muscle, and correction information associated with a first correction mode among the multiple correction modes and correction information associated with a second correction mode differing from the first correction mode among the multiple correction modes differ from each other in at least one of the correction direction and the correction amount.

* * * * *